(12) United States Patent
Borgens et al.

(10) Patent No.: US 7,244,748 B2
(45) Date of Patent: Jul. 17, 2007

(54) PYRIDINES FOR TREATING INJURED MAMMALIAN NERVE TISSUE

(75) Inventors: Richard B. Borgens, Delphi, IN (US); Riyi Shi, West Lafayette, IN (US); Stephen R. Byrn, West Lafayette, IN (US); Daniel T. Smith, Lafayette, IN (US)

(73) Assignee: Purdue Research Foundation, W. Lafayette, IN (US)

( * ) Notice: Subject to any disclaimer, the term of this patent is extended or adjusted under 35 U.S.C. 154(b) by 0 days.

(21) Appl. No.: 10/730,495

(22) Filed: Dec. 5, 2003

(65) Prior Publication Data

US 2004/0171587 A1 Sep. 2, 2004

Related U.S. Application Data

(60) Provisional application No. 60/431,637, filed on Dec. 6, 2002.

(51) Int. Cl.
*A61K 31/44* (2006.01)

(52) U.S. Cl. ............ 514/352; 514/303; 514/340; 546/118; 546/255; 546/309

(58) Field of Classification Search ........... 546/309, 546/22, 118, 123, 153, 183, 255; 514/352, 514/183, 212, 221, 258, 300, 303, 312; 540/460, 540/461, 473, 502, 523, 173; 544/279
See application file for complete search history.

(56) References Cited

U.S. PATENT DOCUMENTS

| | | | |
|---|---|---|---|
| 3,428,642 A * | 2/1969 | Debay et al. | 546/265 |
| 3,433,873 A | 3/1969 | Reinert et al. | |
| 3,804,844 A * | 4/1974 | Pews et al. | 546/309 |
| 3,929,779 A * | 12/1975 | Bickel et al. | 540/227 |
| 3,995,042 A | 11/1976 | Yale et al. | |
| 4,304,911 A | 12/1981 | Zeintz | |
| 5,540,938 A | 7/1996 | Masterson et al. | |
| 5,545,648 A | 8/1996 | Hansebout et al. | |
| 5,700,935 A | 12/1997 | Takenishi et al. | |
| 5,763,463 A * | 6/1998 | Takefuji et al. | 514/352 |
| 5,817,668 A | 10/1998 | Reitz et al. | |
| 5,849,772 A | 12/1998 | Choi et al. | |
| 5,861,309 A | 1/1999 | Bard et al. | |
| 5,880,128 A * | 3/1999 | Doll et al. | 514/253.01 |
| 5,990,109 A * | 11/1999 | Chen et al. | 514/250 |
| 6,200,984 B1 | 3/2001 | Reitz et al. | |
| 6,265,416 B1 * | 7/2001 | Bastian et al. | 514/300 |
| 6,372,768 B2 | 4/2002 | Lowe, III | |
| 6,495,550 B2 | 12/2002 | McNaughton-Smith et al. | |
| 6,632,823 B1 | 10/2003 | Vernier et al. | |
| 6,680,329 B2 * | 1/2004 | Altenburger et al. | 514/318 |
| 6,727,254 B2 * | 4/2004 | Tulshian et al. | 514/252.18 |
| 6,737,423 B2 | 5/2004 | Heinelt et al. | |
| 2002/0045613 A1 * | 4/2002 | Pauls et al. | 514/210.18 |
| 2002/0091265 A1 | 7/2002 | Bos et al. | |
| 2003/0092698 A1 * | 5/2003 | Czekaj et al. | 514/210.17 |
| 2004/0186133 A1 | 9/2004 | Aranyl et al. | |

FOREIGN PATENT DOCUMENTS

| | | | |
|---|---|---|---|
| JP | 3-181462 | * | 8/1991 |
| WO | 01/07436 | * | 2/2001 |

OTHER PUBLICATIONS

Tanga et al., "Syntheses of five potential, etc." CA 127:161747 (1997).*
Shimizu et al., Anticytokinin activity of, etc., CA 112:193716 (1990).*
Kiriazis et al., "Reactions of 2-, 3-, and 4-(N-nitrosomethylamino)pyridine, etc.," CA 112:138873 (1989).*
Sakamoto et al., "Condensed heteroaromatic ring, etc.," CA 108:75166 (1987).*
Von Bebenburg et al., "Substituted polyaminopyridines" CA 93:95098 (1980).*
Yakhontov et al., "Synthesis of isomeric, etc.," CA 69:86786 (1968).*
Imperial Chemical., "Herbicidal compositions" CA 68:59438 (1968).*
Clark-Lewis et al., "Preparation of 3,4-diamino, etc.," CA 57:23142 (1962).*
Takahasi et al., "Pyridine derivatives, etc.," CA 51:12837 (1957).*
Chemical & Engineering News, Feb. 24, 2003, pp. 32-35.*
Gutmann et al. "Phosphoric acid amides" CA 59:9108 (1963).*
Hand et al. "Catalytic reduction . . . " CA 84:74052 (1976).*
Tadzhitdinov et al. "Phosphoric acid . . . " CA 101:23604 (1984).*
Gansel et al. "Distinct sites of action . . . " CA 107:72640 (1987).*
Greensmith et al. "Induction of transmitter release . . . " CA 124:136369 (1996).*
Shi et al. "Differential effects . . . " CA 126:258964 (1997).*
Bundgaard H. "Design of prodrugs" Elsevier, p. 27-33 (1985).*
Stahl et al. "Targeting the central nervous system . . . " Psychopharm. Bull. v.21(3) p. 657-662 (1985).*
Pop et al. "Application of a brain targeting . . . " pharm. Res. v.7(6) 658-664(1990).*
Debay et al. "Carbamates . . . " CA 69:106565 (1968).*
Kano et al. "Effects of ketamine . . . " CA 81:9924 (1974).*

(Continued)

*Primary Examiner*—Celia Chang
(74) *Attorney, Agent, or Firm*—Ice Miller; Homer W. Faucett III; Thomas A. Walsh

(57) ABSTRACT

The invention provides novel pyridines, pharmaceutical compositions comprising such pyridines, and the use of such compositions in treating injured mammalian nerve tissue, including but not limited to an injured spinal cord. In one embodiment, the compounds, compositions, and methods of the instant invention treat a mammalian nerve tissue injury by restoring action potential or nerve impulse conduction through a nerve tissue lesion. Significantly, in vivo application of compounds of the instant invention established, on the basis of SSEP testing, that the compounds provide longer lasting effects at lower concentrations than comparable treatment with the known agent 4-aminopyridine (4 AP).

10 Claims, 8 Drawing Sheets

OTHER PUBLICATIONS

Demenge et al. "Indentification . . . " CA 95:58741 (1981).*
Liu et al. "Potent activation of . . . " CA 142:254331 (2004).*
Matondo, H. et al., "Kinetics of the Hydrolysis of the Potentially Pesticidal N-(4-Pyridyl)carbamates in Micellar Solution", *J. Agric. Food Chem.*, vol. 38, No. 4, pp. 1106-1109, (1990).
Matondo, H. et al., "Synthesis, Mechanism of Action, and Herbicidal Activity of New Aryl", *J. Agric. Food Chem.*, vol. 37, No. 1, pp. 169-172, (1989).

* cited by examiner

PYRIDINES FOR TREATING INJURED MAMMALIAN NERVE TISSUE

CROSS-REFERENCE TO RELATED APPLICATIONS

This application claims priority under 35 U.S.C. § 119(e) to U.S. Provisional Patent Application Ser. No. 60/431,637 filed Dec. 6, 2002, the disclosure of which is hereby incorporated herein by reference.

FIELD OF THE INVENTION

The invention provides novel pyridines, pharmaceutical compositions comprising such pyridines, and methods of using such compositions in treating injured mammalian nerve tissue, including but not limited to an injured spinal cord. In one embodiment, the compounds, compositions, and methods of the instant invention treat a mammalian nerve tissue injury by restoring action potential or nerve impulse conduction though a nerve tissue lesion. Significantly, in vivo application of compounds of the instant invention established, on the basis of SSEP testing, that the compounds provide longer lasting effects at lower concentrations than comparable treatment with the known agent 4-aminopyridine (4 AP). The methods of this invention can be used to promote repair of neuronal damage caused by disease or physical trauma.

BACKGROUND OF THE INVENTION

The biological basis for functional loss after spinal cord injury is the elimination of nerve impulse transmission "up and down" the spinal cord. The basis for a partial functional recovery, independent of how old the injury is, is the restoration of such nerve impulses—in the case of the instant invention, by pharmacological means.

Mechanical damage to the nervous system of mammals results in sometimes irreversible functional deficits. Most functional deficits associated with trauma to both the Peripheral Nervous System (PNS) or Central Nervous System (CNS) result from damage to the nerve fiber or axon, blocking the flow of nerve impulse traffic along the nerve fiber. This may be due to a physical discontinuity in the cable produced by axotomy. The blockage may also occur where the membrane no longer functions as an ionic fence, and/or becomes focally demyelinated [Honmou, O. and Young, W. (1995) Traumatic injury to the spinal axons (Waxman, S. G., Kocsis, J. D., Stys, P. K., Eds.): The Axon, New York: Oxford UP, pp 480–503; Maxwell, W. L. (1996): Histopathological changes at central nodes of ravier after stretch-injury, Microscopy Research and Technique, 34:522–535; Maxwell, W. L., Watt, C., Graham, D I., Gennarelli, L A. (1993): Ultrastructural evidence of axonal shearing as a result of lateral acceleration of the head in non-human primates, Acta Neuropathol, 86:136–144; Maxwell, W. L., Graham, D. I. (1997): Loss of axonal microtubules and neurofilaments after stretch-injury to guinea pig optic nerve fibers, J Neurotrauma, 14:603–614; Blight, A R. (1993): Remyelination, Revascularization, and Recovery of Function in Experimental Spinal Cord Injury (Seil, F. J., Ed.): Advances in Neurobiology: Neural Injury and Regeneration, Vol. 59, New York, Raven Press, pp. 91–103]. In either case, functional deficits occur because of the break in nerve impulse conduction. Even the severe behavioral deficits associated with spinal cord injury is now understood to be largely due to the initial mechanical damage to white matter [Blight, A. R.: Morphometric analysis of a model of spinal cord injury in guinea pigs, with behavioral evidence of delayed secondary pathology, J. Neurolog. Sci., 103:156–171, 1991]. Delayed but progressive episodes of so-called "secondary injury" [Honmou and Young, W. (1995): Traumatic injury to the spinal axons (Waxman, S. G., Kocsis, J. D., Stys, P. K., Eds.): The Axon, New York: Oxford UP pp 480–503; Young, W. (1993): Secondary injury mechanisms in acute spinal cord injury, J. Emerg. Med., 11:13–22.] subsequently enlarge the lesion leading to the typical clinical picture of a cavitated contused spinal cord, and intractable behavioral loss.

Spinal cord injury is a compression injury to the cord even in clinical injuries experienced by humans. The popular notion that the spinal cord is "severed" is largely incorrect, as true anatomical transection of the spinal cord is quite rare in human injuries. After the injury, there is a variable amount—or "rind"—of spinal cord white matter left intact. However, this region of anatomically intact nerve fibers does not function. In particular, this local region (usually less than 1 vertebral segment in extent) does not conduct nerve impulses through the region of damage. This is believed to be due to demyelination, as well as other factors. The loss, or the reduced thickness of myelin, which insulates the nerve process, causes conduction blockage at the Nodes of Ranvier. This is because so-called "voltage gated" fast potassium channels are localized at paranodal regions in myelinated nerve fibers underneath an insulating layer of myelin. When myelin retracts or is lost after injury, the clusters of potassium channels are exposed to extracellular fluids and are also deprived of their electrical insulation. Potassium loss though these naked channels both increases the extracellular concentration of potassium, and helps extinguish a nerve impulse (actually a depolarization of this local nerve membrane). Indeed, it is well known that the extracellular microenvironment near a spinal injury is rich in potassium, which by itself dampens the ability of nervous tissue to function normally. Eidelberg, et al., (1975), Immediate consequences of spinal cord injury: Possible role of potassium in axonal conduction block, Surg Neurol 3:317–321.

Moreover, the loss of the electrical insulating capacity of myelin facilitates short circuit potassium current that aids in extinguishing the nerve impulse before it can begin to cross the nodal region. Blight A. R. (1993), "Remyelination, revascularization, and recovery of function in experimental spinal cord injury", Seil F. J. (ed) Advances in neurobiology: Neural injury and regeneration (vol) 59 pp 91–103. Drugs that block this exodus of potassium from inside the nerve fiber to the outside milieu (so called channel blockers) are believed to be the biological basis for the restoration of action potential (or nerve impulse) conduction through spinal lesions associated with variable recoveries of functions in human patients. Hayes K. C., et al. (1993) Pre-clinical trial of 4-Aminopyridine in patients with chronic spinal cord injury, Paraplegia 31:216–224; Hayes K. C. (1994) 4-Aminopyridine and spinal cord injury: A review, Restor Neurol Neurosci 6:259–270; Hansebout R. R., Blight et al. (1993) 4-Aminopyridine in chronic spinal cord injury: A controlled, double-blind, crossover study in eight patients. J Neurotrauma 10:19–24. The only drug of this type, 4-Aminopyridine (the "time release" form of the drug is called Fampridine), has shown promise in restoring nerve function in paralyzed persons. However, clinically meaningful recoveries of function only occur in about 30% of the treated population, and in the balance, these recoveries are associated with numerous unwanted side effects that occur at the concentrations of the drug required. Such unacceptable side effects include dizziness mid loss of balance at one end of a scale—to the possibility of seizures at the other.

This problem is of such magnitude that infusions of 4 AP directly into the cerebrospinal fluid have been applied in dogs, Pratt K., et al., (1995) Plasma and cerebral spinal fluid concentrations of 4-Aminopyridine following intravenous injection and metered intrathecal delivery in canines, J Neurotrauma 12:23–39, and has been recently tried in six human patients. Halter J. A., et al. (2000) Intrathecal administration of 4-Aminopyridine in chronic spinal injured patients, Spinal Cord 12:7828–232. This would theoretically provide high concentrations of the drug directly at the spinal cord lesion, eliminating high concentrations in the blood. While such intrathecal administration is possible, it requires extensive and complicated surgery to implant special pumps and to cannulate the damaged spinal cord. The need exists, therefore, for improved compounds, pharmaceutical compositions, and methods that are useful in the treatment of spinal injury and that do not suffer from the aforementioned drawbacks. In particular, there is a need for compounds, compositions, and methods which will reduce the damaging effect of a traumatic injury to mammalian CNS tissue, especially spinal tissue, by in vivo treatment thereof.

OBJECTS OF THE INVENTION

It is an object of the instant invention to provide novel compounds, pharmaceutical compositions, and methods useful in treating injured mammalian nerve tissue, including but not limited to an injured spinal cord.

It is a further object of the instant invention to provide novel compounds, pharmaceutical compositions and methods that are useful in treating injured mammalian nerve tissue, including but not limited to an injured spinal cord and that restore action potential or nerve impulse conduction through lesions.

It is a further object of the instant invention to provide compounds, compositions, and methods which will reduce the damaging effect of a traumatic injury to mammalian nerve tissue, especially spinal tissue, by in vivo treatment thereof.

It is a further object of the instant invention to provide compounds, compositions, and methods which will stimulate growth or proliferation of nerve tissue.

It is a still further object of the instant invention to provide novel compounds, pharmaceutical compositions and methods that are useful in treating injured mammalian nerve tissue, including but not limited to an injured spinal cord, that are free of unwanted side effects, and that can be readily administered to a subject in need.

SUMMARY OF THE INVENTION

In accordance with the above-stated objects, the instant invention provides novel substituted pyridines, pharmaceutical compositions comprising such pyridines, and methods of using such pyridines in treating injured mammalian nerve tissue, including but not limited to an injured spinal cord. In one embodiment, the compounds, compositions, and methods of the instant invention treat a mammalian nerve tissue lesion by restoring action potential or nerve impulse conduction through the nerve tissue lesion. Significantly, in vivo application of compounds of the instant invention revealed, on the basis of SSEP testing defined hereinafter, that the compounds provide longer lasting effects at a lower concentration than comparable treatment with the known agent 4 AP. The compounds, upon in vivo administration, reduced the deleterious effect of traumatic CNS tissue injury though restoration of nerve impulse conduction through nerve tissue lesions.

The compounds, compositions, and methods of the instant invention are relatively free of unwanted side effects and can be readily administered to a subject in need. Substituted pyridines of the instant invention show a previously unrecognized potassium channel blocking activity, can be safely delivered to mammals, work at lower concentrations than the known agent 4 AP, and are effective in a single dosage application for an extended period of dine. Examples of pyridines of the instant invention are provided by the following formula (I). It should be appreciated that pharmaceutically acceptable salts, solvates, and polymorphs of the pyridines of the present invention are also contemplated.

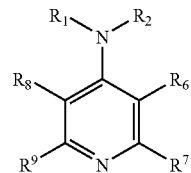

where $R^1$ is H or a $C_1$–$C_4$ alkyl group;

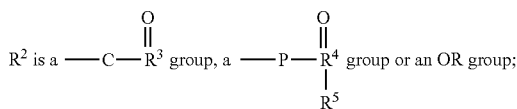

$R^3$ is H, a $C_1$–$C_{20}$ alkyl group, an OR group, an alkylene ester group

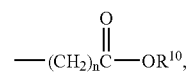

an amine group —$NR^{11}R^{12}$ or a —$(CH_2)_m$-group where m is 1–3 and forms a ring with $R^6$, R is a $C_1$–$C_{20}$ alkyl group (preferably a $C_1$–$C_6$ alkyl group), an aryl (preferably phenyl) group or an alkylene aryl group (where the alkylene group is a $C_1$–$C_{20}$ alkylene group, preferably a $C_1$–$C_3$ alkylene group, and the aryl group is preferably a phenyl group), $R^{10}$ is a $C_1$–$C_{10}$ alkyl group (preferably, a $C_1$–$C_3$ alkyl group), n is 1 to 20 (preferably 1 to 3), $R^{11}$ is selected from H, $C_1$–$C_4$ alkyl, aryl, alkylene aryl (wherein the alkylene group is up to 20 carbon units in length and the aryl group is preferably phenyl) or an alkylene ester group as described above, and $R^{12}$ is selected from H, $C_1$–$C_4$ alkyl, aryl, alkylene aryl (wherein the alkylene group is up to 20 carbon units in length and the aryl group is preferably phenyl) or an alkylene ester group as described above or is a —$(CH_2)_z$-group where z is 0 to 2, such that $R^{12}$ forms a ring with $R^6$ to form a ring, and preferably wherein when one of $R^{11}$ and $R^{12}$ is other than H, the other of $R^{11}$ or $R^{12}$ is H; $R^6$ is H, $C_1$–$C_4$ alkyl, F, Cl, Br, I, $NO_2$ or a $NR^{13}R^{14}$ group where $R^{13}$ is H or a $C_1$–$C_3$ alkyl group and $R^{14}$ is a —$(CH_2)m$— group where m is 1 to 3 and forms a ring with the

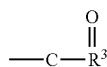

group when $R^3$ is absent; and each of $R^7$, $R^8$ and $R^9$ is independently selected from H, $C_1$–$C_4$ alkyl, F, Cl, Br, I or $NO_2$, preferably, at least two, and more preferably three of $R^7$, $R^8$ and $R^9$ are H.

The present invention includes the pharmaceutically acceptable acid addition salts of compounds of the formula (I). The acids which are used to prepare the pharmaceutically acceptable acid addition salts of the aforementioned base compounds of this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylenebis(2-hydroxy-3 naphthoate)] salts.

The invention also includes base addition salts of formula (I). The chemical bases that may be used as reagents to prepare pharmaceutically acceptable base salts of those compounds of formula (I) that are acidic in nature are those that form non-toxic base salts with such compounds. Such non-toxic base salts include, but are not limited to those derived from such pharmacologically acceptable cations such as alkali metal cations (e.g., potassium and sodium) and alkaline earth metal cations (e, calcium and magnesium), ammonium or water-soluble amine addition salts such as N-methylglucamine-(meglumine), and the lower alkanolammonium and other base salts of pharmaceutically acceptable organic amines.

The compounds of this invention include all stereoisomers (i.e., cis and trans isomers) and all optical isomers of compounds of the formula (I) (e.g., R and S enantiomers), as well as racemic, diastereomeric and other mixtures of such isomers, as well as all polymorphs of the compounds.

The compounds of this invention may contain olefin-like double bonds. When such bonds are present, the compounds of the invention exist as cis and trans configurations and as mixtures thereof.

Unless otherwise indicated, the alkyl and alkenyl groups referred to herein, as well as the alkyl moieties of other groups referred to herein (e.g., alkoxy), may be linear or branched, and they may also be cyclic (e.g., cyclopropyl, cyclobutyl, cyclopentyl, or cyclohexyl) or be linear or branched and contain cyclic moieties. Unless otherwise indicated, halogen includes fluorine, chlorine, bromine, and iodine.

The present invention also relates to a method for treating injured mammalian nerve tissue, especially injured human nerve tissue, including reducing the deleterious effect of CNS or PNS tissue injury, comprising administering to a mammal, preferably a human, requiring such treatment an effective amount of a compound of the formula (I) or a pharmaceutically acceptable salt, solvate, or polymorph thereof.

The present invention also relates to a pharmaceutical composition for treating injured mammalian nerve tissue, especially injured human nerve tissue, including reducing the deleterious effect of CNS or PNS tissue injury, comprising:

(a) a pharmaceutically acceptable carrier; and
(b) a compound of the formula (I) or a pharmaceutically acceptable salt, solvate, or polymorph thereof.

wherein the amount of the active compound (i.e., the compound of formula (I), or a pharmaceutically acceptable salt, solvate, or polymorph thereof) is such that the composition is effective in treating injured mammalian nerve tissue ,including reducing the deleterious effects of CNS or PNS tissue injury.

The present invention also relates to a method of reducing the deleterious effect of CNS or PNS tissue injury, and treating an associated nerve tissue lesion, by restoring action potential or nerve impulse conduction through the nerve tissue lesion by in vivo administration of an effective amount of a compound of the formula (I), or a pharmaceutically acceptable salt, solvate, or polymorph thereof.

The compounds and pharmaceutical compositions of the instant invention may be applied as neurotrophic factors. The term "neurotrophic factor", as used herein, refers to compounds which are capable of stimulating growth or proliferation of nervous tissue. In this regard, they may be administered alone or with known neurotrophic factors including, but are not limited to, nerve growth factor (NGF), insulin growth factor (IGF-1) and its active truncated derivatives such as gIGF-1, acidid and basic fibroblast growth factor (aFGF and bFGF, respectively), platelet-derived growth factors (PDGF), brain-derived neurotrophic factor (BDNF), ciliary neurotrophic factors (CNTF), glial cell line-derived neurotrophic factor (GDNF), neurotrophin-3 (NT-3) and neurotrophin 4/5 (NT-4/5).

In vitro testing of compounds of the instant invention has demonstrated that they exhibit not only potassium channel blockade properties, but serve to specifically excite neural circuits in general. Further, in vivo testing established the effectiveness of these compounds in restoring nerve impulse conduction through damaged regions of the spinal cord white matter (comprised solely of nerve fibers). Somatosensory evoked potential testing (SSEP), which reveals the ability of the spinal cord to propagate ascending evoked volleys of nerve impulses through a lesion, which are then recorded at the brain (as explained further hereinafter), established in vivo recovery of SSEP exceeding 20% of the normal SSEP (pre-injury), as well as exceeding the magnitude of recovery of a similar SSEP recovery induced by 4 AP. Significantly, in vivo application of compounds of the instant invention revealed, on the basis of SSEP testing, that these compounds, in only one application, provide longer lasting effects at a lower concentration than comparable 4 AP treatment.

Additional aspects of the instant invention are presented in the following detailed description.

DETAILED DESCRIPTION OF THE INVENTION

As used herein, the following terms have the following respective meanings. "4 AP" means 4-aminopyridine.

"Double sucrose gap isolation and recording chamber" is a novel means used in testing compound action potential propagation through a standardized crush lesion to strips of guinea pig spinal cord white matter in organ culture. The biological basis for the loss of behavior after spinal cord injury is the interruption of nerve impulse "traffic" ascending the cord to the brain from nerve "inputs" from the body, and the reverse—loss of impulse traffic arising in the brain "descending" the spinal cord to targets in the body. Thus, this test vehicle is a first evaluation of the crucial and relevant biological basis for paralysis. The double sucrose gap chamber is an exceptional means to "prescreen" numerous pharmacological interventions prior to the more arduous and time consuming means of testing similar functioning in the "whole" animal independent of other practical considerations such as the best route of administration (for example intravenous or oral administration) that can only be evaluated in animal testing.

Figure 6:
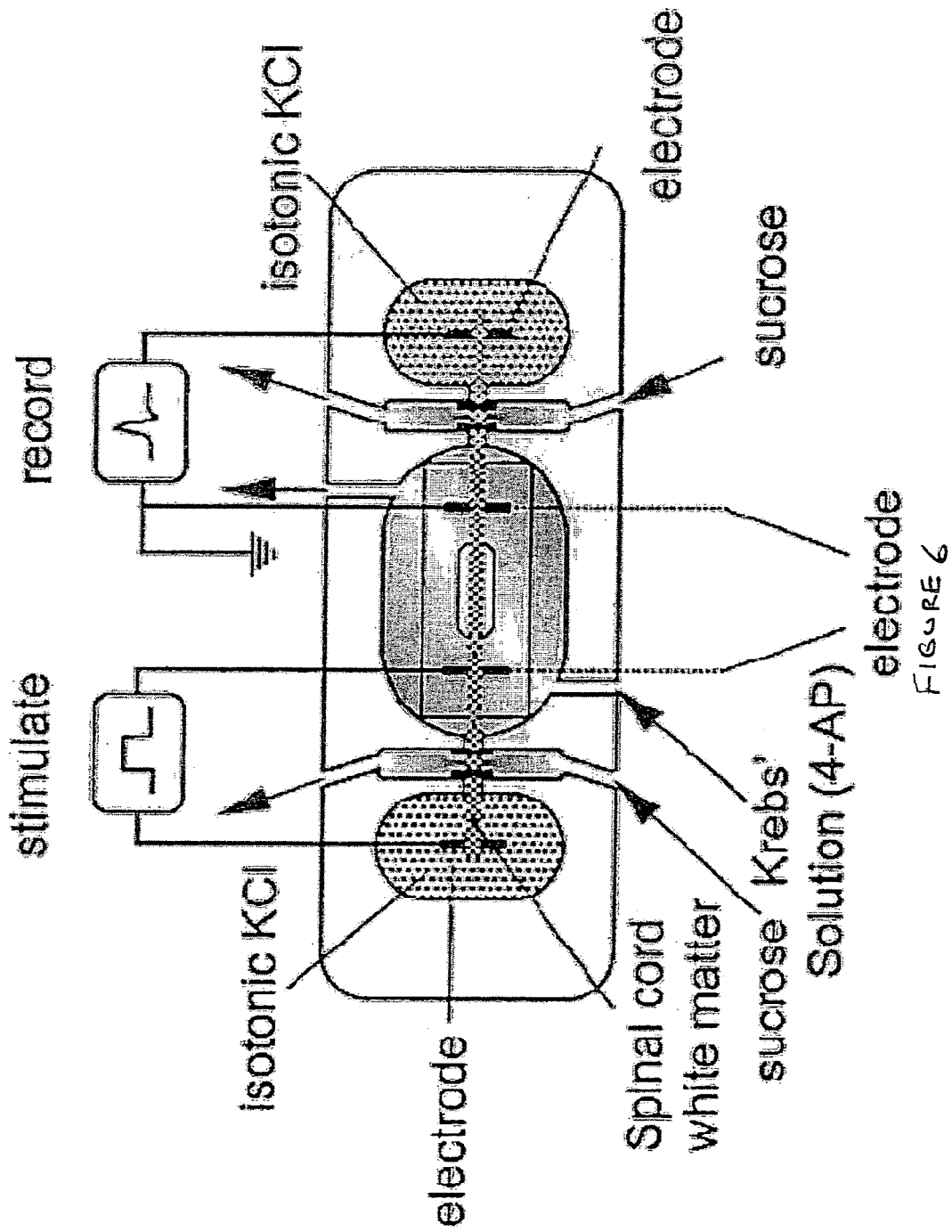
FIG. 6 illustrates a double sucrose gap isolation and recording chamber used to test compound action potential propagation through a standardized crush lesion to strips of guinea pig spinal cord white matter in organ culture.

As shown in FIG. 6, the isolated spinal cord (stippled band) is shown mounted in the chamber, with the central well continuously perfused with oxygenated Krebs solution (similar to extracellular fluid). The test drugs were added to this chamber. The two ends of the spinal cord lie in separate wells filled with isotonic KCl (similar to intracellular fluid) divided from the central well by narrow gaps filled with flowing, isotonic sucrose solution. Electrodes were formed from Ag/AgCl wires. Action potentials were generated through a pair of electrodes at the left hand sucrose gap, conducted through the central part of the spinal cord and recorded by another pair of electrodes in the right-hand gap by conventional bridge amplification techniques. A compression to the cord is performed at its approximate midpoint, within the central Krebs solution containing chamber. This then interferes with conduction of compound action potentials through the cord to the pair of recording electrodes on the far side.

As indicated above, a strip of isolated spinal cord white mailer (obtained from adult guinea pigs), approximately 35–40 mm in length, is placed in the chamber and continuously superfused with oxygenated Krebs' solution (c. 2 ml/mm) by means of a peristaltic pump. The free ends of the spinal cord strip are placed across the sucrose gap channels to side compartments filled with isotonic (120 mM) potassium chloride. The temperature of the chamber is maintained with a Peltier unit in the base, thermostatically controlled with a thermistor system (Cambion Instruments). The axons are stimulated and compound action potentials, as well as compound membrane potential (in the form of gap potential) are recorded at opposite ends of the strip of white matter by silver/silver chloride wire electrodes positioned within the side chambers and the central bath. The central bath is connected to instrument ground. Stimuli are delivered through stimulus isolation units and are usually in the form of 0.1 msec constant current unipolar pulses. Recordings are made using a bridge amplifier and Neurocorder (both from Neurodata Instruments Inc.) for digital data storage on videotape. Subsequent analysis are performed using custom Labview® software (National Instruments) on a Macintosh Power PC G3 computer. These procedures, along with construction of the double sucrose gap chamber are described in Moriarty, L. J.; Duerstock, B. S.; Bajaj, C. L.; Lin, K.; Borgens, R. B. Two and Three Dimensional Computer Graphic Evaluation of the Subacute Spinal Cord Injury. *J. Neurologic. Sci.* 1998, 155, 121–137; Borgens, R. B.; Shi, R.; Bohner, T. D. Behavioral Recovery from Spinal Cord Injury Following Delayed Application of Polyethylene Glycol. *Journal of Experimental Biology* 2002, 205, 1–12 which are both incorporated herein by reference.

"Effective amount" when used herein with reference to a novel pyridine of the instant invention denotes a quantity of the compound which, when administered to a patient or subject, is sufficient to result in a measurable improvement in electrical and/or behavioral function of a nerve which has been so damaged or injured that normal functioning is not possible. As discussed below, the efficacy of the treatment may be determined in a variety of ways, including methods which detect restoration of nerve function. With respect to the use of the term "effective amount" with other agents, for example, 4 AP, that term is used to describe an amount of an agent effective within the context of that agent's use in the present invention.

"Nerve tissue" as used herein refers to any vertebrate nerve tissue, particularly including mammalian cells of the central nervous system (CNS) and peripheral nervous system (PNS). More particularly, nerve tissue includes spinal cord neuronal structures, peripheral nervous system nerves, and even nerve cells of the brain.

"Nerve tissue injury", "injured mammalian nerve tissue", or "CNS or PNS nerve tissue injury" include any damage to relevant nerve tissue irrespective of cause, e.g., injuries attributable to trauma including but not limited to nerve tissue lesions, traumatically-induced compression, tumors, hemorrhage, infectious processes, spinal stenosis, or impaired blood supply.

"Treating injured mammalian nerve tissue" includes, but is not limited to, the in vivo administration of compounds, compositions, and methods of the instant invention to restore action potential or nerve impulse conduction through a nerve tissue lesion. The term may also include such administration in an effort to reduce the damaging effects of any injury to mammalian nerve tissue, whether through restoration of action potential or nerve impulse conduction, by stimulating growth or proliferation of nervous tissue, by ameliorating unwanted conditions in the extracellular microenvironment near an injury, or otherwise.

"Neurotrophic factor", as used herein, refers to compounds which are capable of stimulating growth or proliferation of nervous tissue, including compounds of the instant invention and known neurotrophic factors described previously herein.

Figure 2:
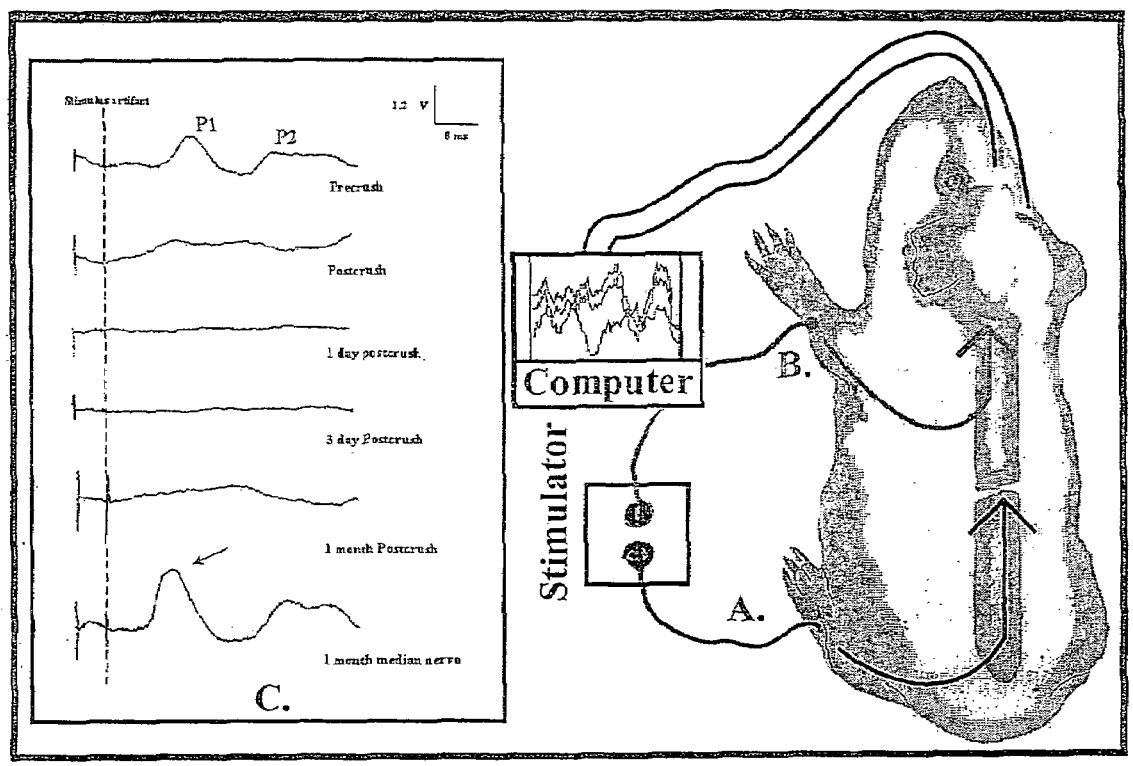
FIG. 2 illustrates a SSEP testing protocol used to test compounds of the instant invention in vivo and reflects normal recordings in intact animals, the elimination of sensory impulses after a mid-thoracic spinal cord injury, and the importance of a median nerve control procedure.

"Somatosensory evoked potential testing (SSEP)" is a means of measuring ascending nerve impulse "traffic" in a "whole" animal. SSEP reveals the ability of the spinal cord to propagate ascending evoked volleys of nerve impulses through a lesion, which are then recorded at the brain. These volleys of evoked potentials are initiated by electrical stimulation of the tibial nerve of the hind leg of an animal, which induces ascending sensory volleys of nociceptive impulses to the contralateral sensory cortex of the brain in the intact animal. A severe spinal cord injury eliminates the ability of evoked potentials to cross the lesion and thus SSEPs are not recorded at the brain after lesioning. Quantitative evaluation of the recovery of SSEP conduction through the whole animal provides a more relevant indicator of the feasibility of these compounds to be useful in reversing behavioral loss after specific, localized, and standardized CNS injury. To eliminate the possibility that the failure to record SSEPs could be due to other factors, a control recording is carried out using the median nerve of the foreleg. Since this neural circuit is completely intact (that is—"above" the level of the spinal injury) normal SSEPs must be obtained after such "control" stimulation. FIG. 2 is a diagram of this testing protocol and provides examples of normal recordings in intact animals, the elimination of sensory impulses after a mid-thoracic spinal cord injury, and explains these issues in detail, as well as, emphasizing the importance of a median nerve control procedure.

"Tracks", "Long Tracks", and "CAPS" have the following meaning. In the spinal cord (independent of the brain), long unbroken bundles (called "tracts") of nerve fibers carry nerve impulses sometimes over the entire length of the cord, both ascending and descending it ("long tracts"). The nerve impulses carried in such "long tracts" (such as the dorsal column pathway, the spinothalamic tract, etc.) are CAPs. In the whole animal, nerve impulses stimulated, for example by a painful stimuli applied to the foot, ascend the cord all the way to the brain—to the somatosensory region of the brain's Sensory Cortex. While the CAPS traveling up the cord to the hind brain may not have synapses mediating conduction from one nerve to the next nerve—getting from the hindbrain to the Cortex is a very different matter—where hundreds of synapses "relay" nerve impulse from one brain neuron to the next in its various regions to end at the sensory cortex. Here is where the painful stimulus applied at the foot is finally appreciated in consciousness. These ascending CAPS together with synaptic transmission through the brains complex neural circuits are called "Evoked Potentials" in contrast to CAPs. CAPs are measured through limited regions of spinal cord white matter, while evoked potentials represent conduction though the entire animal. A spinal cord injury interrupts CAP conduction through the cord (FIG. 1) but of course, it also eliminates conduction through the spinal cord in the entire animal.

I. Synthesis of Novel Pyridines

Figure 4:
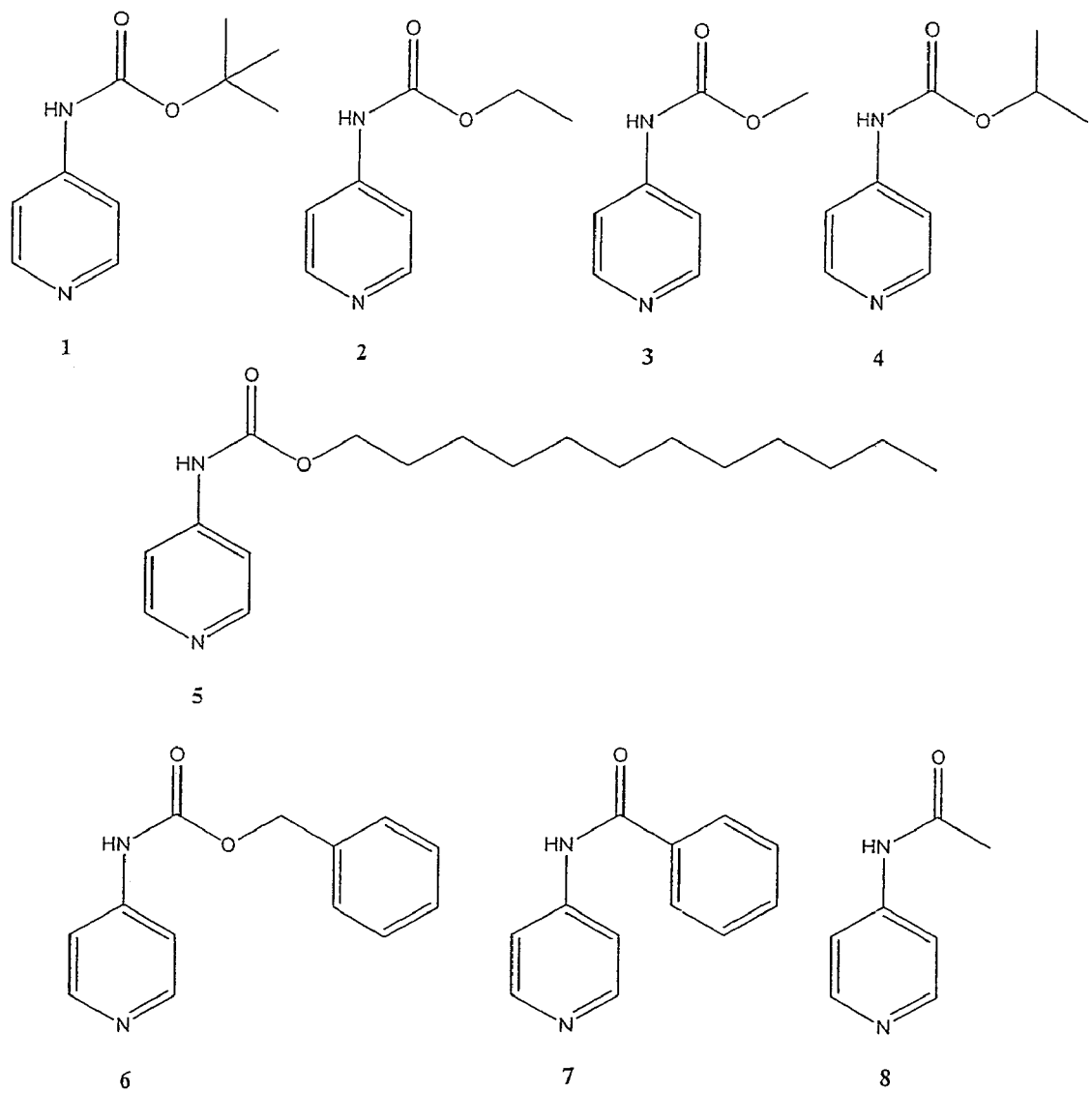
FIG. 4 illustrates the structural formulae of certain examples of pyridine derivatives of the instant invention.
Figure 5:
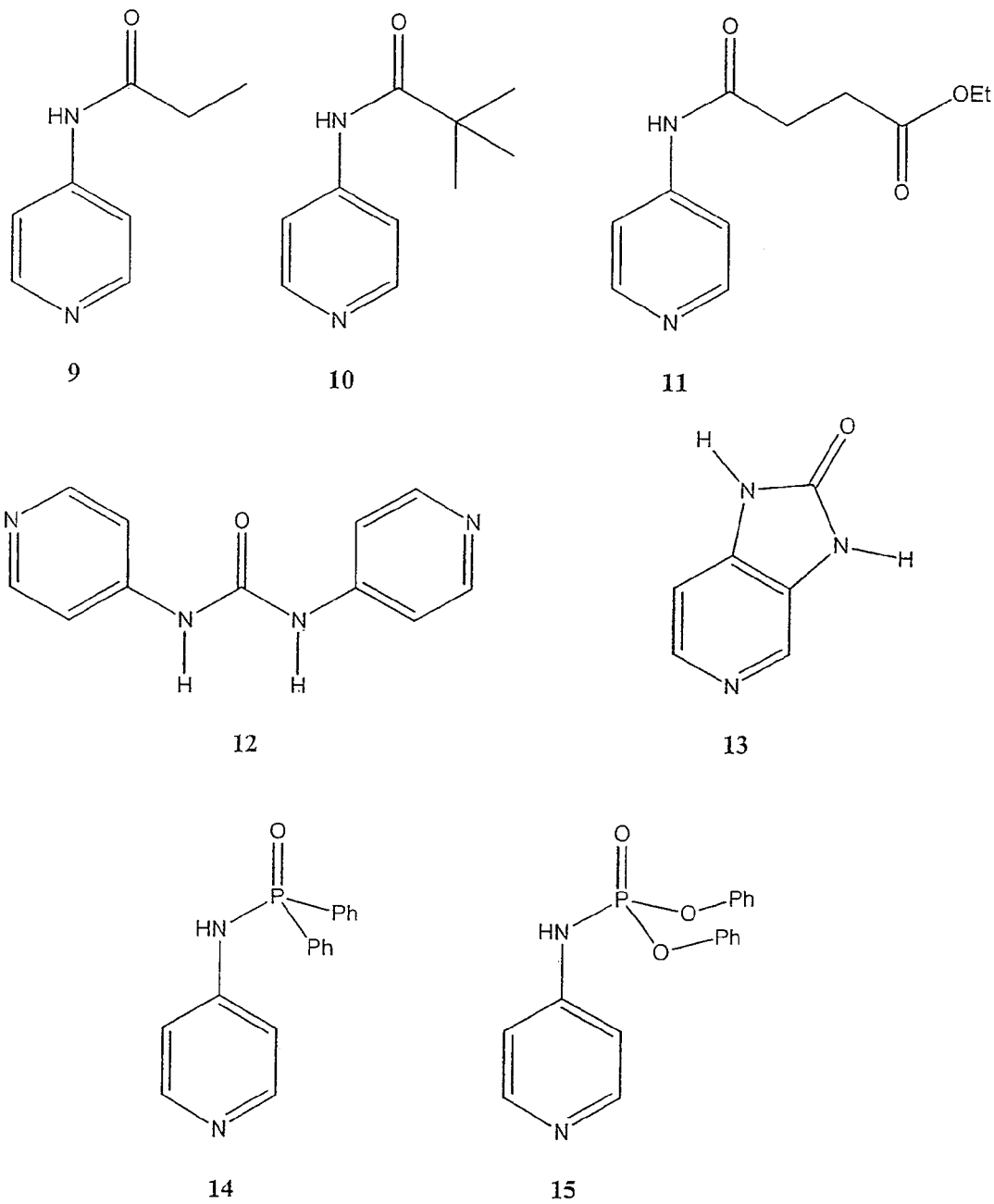
FIG. 5 illustrates the structural formulae of additional examples of certain pyridine derivatives of the instant invention.

The synthesis of representative compounds of the instant invention, the structural formulae of which are illustrated in FIGS. 4 and 5, was accomplished as set forth in detail below. However, it will be appreciated that other derivatives of, and substitutions to, novel pyridines of formula (I) are also within the scope of this invention.

The starting materials for these representative compounds of formula (I) are either commercially available or known in the art. For example, 4-(Methylamino)pyridine was purchased from Lancaster Synthesis. 4-(Dimethylamino)pyridine was purchased from Sigma-Aldrich, Milwaukee, Wis. The following amides and ureas were synthesized using conventional methods, for example, described in Ghosh, S.; Krishnan, A.; Das, P. K. Ramakrishnan, S. Determination of Critical Micelle Concentration by Hyper-Rayleigh Scattering. *J. Am. Chem. Soc.* 2003, 125, 1602–1606: Kato, T.; Yamamoto, Y.; Takeda, S. Ketene and Its Derivatives. IV. Reaction of Primary Amine with Ketene Acetals. Yakugaku Zasshi 1973, 93(8), 1034–1042: Meanwell, N. A; Sit, S. Y.; Gao, J.; Wong, H. S.; Gao, O.; St. Laurent, D. R.; Balasubramanian, N. Regiospecific Functionalization of 1,3-Dihydro-2H-benzimidazol-2-one and Structurally Related Cyclic Urea Derivatives. *J. Org. Chem.* 1995, 60, 1565–1582: Kovalenko, A. L.; Serov, Y. V.; Nikonov, A. A.; Tselinskii, I. V. Aminomethylation of N,N'- and N,N,N'-Substituted Ureas with N-Methylene-tert-butylamine. *Zhur. Org. Khim.* 1991, 27(10), 2074–2077, all of which are incorporated herein by reference.

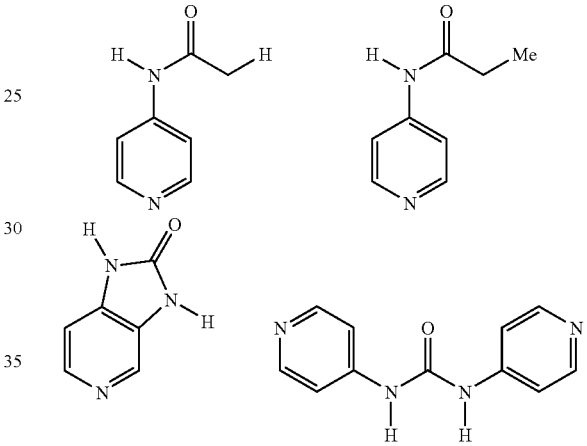

The following carbamates were synthesized from 4-AP.

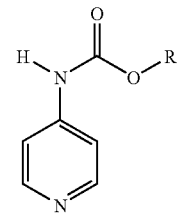

R = Me, Et, or t-Bu

4-AP was purchased from Richman Chemical Co., Lower Gwynedd, Pa. All reagents were used as received without further purification. Melting points were determined in capillary tubes using a Thomas Hover melting point apparatus and are uncorrected. NMR spectra were obtained on a Bruker ARX-300 instrument using the indicated solvent.

Synthesis of N-(4-Pyridyl) t-Butyl Carbamate (1). To a solution of 4-aminopyridine (50.0 g, 531 mmol) in triethylamine/CH$_2$Cl$_2$ (1:1, 200 mL) at 0° C. was slowly added a solution of di-t-butyl-dicarbonate (116 g, 531 mmol) in CH$_2$Cl$_2$ (150 mL). The resulting mixture was allowed to warm to rt overnight then was concentrated. The crude product was taken up in hot EtOAc, filtered and precipitated with hexanes. The precipitate was collected by filtration, washed with hexanes and dried under vacuum to give 91.0 g (88% yield) of pure t-butyl carbamate. Mp=147–148° C. $^1$H NMR (300 MHz, CDCl$_3$) δ 8.97 (s, 1 H, N-H); 8.39 (d, J=5.2 Hz, 2 H, Ar); 7.41 (d, J=5.2 Hz, 2 H, Ar); 1.46 (s, 9 H, t-Bu). $^{13}$C NMR (75 MHz, CDCl$_3$) δ 153.1 (C=O); 150.3 (Ar); 147.3 (Ar); 113.0 (Ar); 81.5 (O—C—R$_3$); 28.6 (Me). Anal. Calc'd for C$_{10}$H$_{14}$N$_2$O$_2$ (MW=194.23): C=61.84, H=7.27, N=14.42. Found: C=61.60, H=7.05, N=14.50.

Synthesis of N-(4-Pyridyl) Ethyl Carbamate (2). To a solution of 4-aminopyridine (20.0 g, 212 mmol) in CH$_2$Cl$_2$ (200 mL) at 0° C. was added triethylamine (30.0 mL, 212 mmol) and ethyl chloroformate (20.3 mL, 212 mmol). The resulting mixture was allowed to warm to rt overnight then was concentrated. The solid products were slurried with saturated aqueous NaHCO$_3$, stirred for 1 h, concentrated and dried under vacuum. The crude product was slurried with hot MeOH (500 mL) for 1 h, filtered and the filtrate was concentrated. The crude carbamate was recrystallized from toluene/hexanes to give 31.8 g (90% yield) of pure ethyl carbamate. Mp=127–128° C. $^1$H NMR (300 MHz, CDCl$_3$) δ 10.02 (s, 1 H, N-H); 8.56 (d, J=6.2 Hz, 2 H, Ar); 7.63 (d, J=6.2 Hz, 2 H, Ar); 4.33 (q, J=7.1 Hz, 2 H, OCH$_2$); 1.38 (t, J=7.1 Hz, 3 H, Me). $^{13}$C NMR (75 MHz, CDCl$_3$) δ 154.3 (C=O); 150.2 (Ar); 147.3 (Ar); 113.3 (Ar); 61.8 (OCH$_2$); 14.8 (Me). Anal. Calc'd for C$_8$H$_{10}$N$_2$O$_2$ (MW=166.18): C=57.82, H=6.07, N=16.86. Found: C=58.01, H=5.92, N=16.62.

Synthesis of N-(4-Pyridyl) Methyl Carbamate (3). To a solution of 4-aminopyridine (20.0 g, 212 mmol) in CH$_2$Cl$_2$ (200 mL) at 0° C. was added triethylamine (30.0 mL, 212 mmol) and methyl chloroformate (16.4 mL, 212 mmol). The resulting mixture was allowed to warm to rt overnight then was concentrated. The solid products were slurried with saturated aqueous NaHCO$_3$, stirred for 1 h, concentrated and dried under vacuum. The crude product was then slurried with hot MeOH (500 mL) for 1 h, filtered and the filtrate was concentrated. The crude carbamate was recrystallized from toluene/hexanes to give 15.5 g (48% yield) of pure methyl carbamate.

The following procedure may also be used to synthesize N-(4-Pyridyl) Methyl Carbamate (3): To a solution of 4-aminopyridine (15.0 g, 160 mmol) in CH$_2$Cl$_2$ (200 mL) at 0° C. was added triethylamine (30.0 mL, 212 mmol) then methyl chloroformate (15.0 mL, 192 mmol). The crude carbamate was recrystallized from water to give 15.9 g (66% yield) of pure methyl carbamate 12. Mp=168–170° C. $^1$H NMR (300 MHz, MeOH-d$_4$) δ 8.49 (d, J=6.5 Hz, 2 H, Ar); 7.67 (d, J=6.5 Hz, 2 H, Ar); 5.22 (br s, 1 H, N-H); 3.94 (s, 3 H, OMe). $^{13}$C NMR (75 MHz, MeOH-d$_4$) δ 156.0 (C=O); 151.0 (Ar); 149.2 (Ar); 114.3 (Ar); 53.3 (OMe). Anal. Calc'd for C$_7$H$_8$N$_2$O$_2$ (MW=152.15): C=55.26, H=5.30, N=18.41. Found: C=55.29, H=5.31, N=18.20.

Synthesis of N-(4-Pyridyl) Isopropyl Carbamate (4). To a solution of 4-aminopyridine (2.00 g, 21.2 mmol) in CH$_2$Cl$_2$ (50 mL) at 0° C. was added triethylamine (3.50 mL, 25.0 mmol) and isopropyl chloroformate (22.0 mL, 1.0 M in toluene). The ice bath was removed and the resulting mixture was allowed to warm to rt over 2 h. The reaction mixture was filtered through a plug of silica gel (EtOAc) then concentrated. The crude product was recrystallized from EtOAc to give 1.90 g (50% yield) of pure isopropyl carbamate.

Synthesis of N-(4-Pyridyl) Dodecyl Carbamate (5). To a solution of 4-aminopyridine (3.00 g, 31.9 mmol) in CH$_2$Cl$_2$ (50 mL) at 0° C. was added triethylamine (5.60 mL, 40.0 mmol) and dodecyl chloroformate (8.70 g, 35.0 mmol). The ice bath was removed and the resulting mixture was allowed to warm to rt over 3 h before being poured into saturated aqueous NaHCO$_3$. The product was extracted with CH$_2$Cl$_2$, washed with brine, dried (MgSO$_4$) and concentrated. The crude product was recrystallized from EtOAc/hexanes to give 8.80 g (90% yield) of pure dodecyl carbamate.

Synthesis of N-(4-Pyridyl) Benzyl Carbamate (6). To a solution of 4-aminopyridine (2.00 g, 21.2 mmol) in CH$_2$Cl$_2$ (30 mL) at 0° C. was added triethylamine (3.50 mL, 25.0 mmol) and benzyl chloroformate (3.10 mL, 22.0 mmol). The ice bath was removed and the resulting mixture was allowed to warm to rt overnight before being poured into saturated aqueous NaHCO$_3$. The product was extracted with CH$_2$Cl$_2$, dried (Na$_2$SO$_4$) and concentrated. The crude product was recrystallized from EtOAc to give 2.90 g (60% yield) of pure benzyl carbamate.

Synthesis of N-(4-Pyridyl) Benzamide (7). To a solution of 4-aminopyridine (3.00 g, 31.9 mmol) in CH$_2$Cl$_2$ (50 mL) at 0° C. was added triethylamine (6.70 mL, 47.9 mmol) and benzoyl chloride (3.70 mL, 31.9 mmol). The ice bath was removed and the resulting mixture was allowed to warm tort over 1.5 h. The reaction was quenched with saturated aqueous NaHCO$_3$, extracted with CH$_2$Cl$_2$, washed with brine, dried (MgSO$_4$) and concentrated. The crude product was recrystallized from EtOAc/hexanes to give 4.73 g (75% yield) of pure benzamide.

Synthesis of N-(4-Pyridyl) Acetamide (8). To a solution of 4-aminopyridine (2.00 g, 21.2 mmol) in CH$_2$Cl$_2$ (30 mL) at 0° C. was added triethylamine (3.60 mL, 25.6 mmol) and acetic anhydride (2.20 mL, 23.2 mmol). The ice bath was removed and the resulting mixture was allowed to warm to rt overnight before being poured into saturated aqueous NaHCO$_3$. The mixture was stirred for 15 min then the layers were separated. The aqueous layer was extracted with CH$_2$Cl$_2$ twice more in the same fashion. The combined organic layers were dried (Na$_2$SO$_4$) and concentrated. The crude product was recrystallized from EtOAc to give 1.60 g (56% yield) of pure acetamide.

Synthesis of N-(4-Pyridyl) Propionamide (9). To a solution of 4-aminopyridine (3.00 g, 31.9 mmol) in CH$_2$Cl$_2$ (30 mL) at 0° C. was added triethylamine (6.70 mL, 47.8 mmol) and propionyl chloride (3.30 mL, 38.2 mmol). The ice bath was removed and the resulting mixture was allowed to warm to rt over 4 h before being poured into saturated aqueous NaHCO$_3$. The mixture was stirred for 45 min and was filtered. The filter cake was recrystallized from EtOAc to give 1.65 g (50% yield) of pure propionamide.

Synthesis of N-(4-Pyridyl) Trimethylacetamide (10). To a solution of 4-aminopyridine (2.00 g, 21.2 mmol) in CH$_2$Cl$_2$ (30 mL) at 0° C. was added triethylamine (3.50 mL, 25.0 mmol) and pivaloyl chloride (2.70 mL, 23.2 mmol). The ice bath was removed and the resulting mixture was allowed to warm to rt overnight before being poured into saturated aqueous NaHCO$_3$. The mixture was stirred for 5 min then the layers were separated. The aqueous layer was extracted with CH$_2$Cl$_2$ twice more in the same fashion. The combined organic layers were dried (Na$_2$SO$_4$) and concentrated. The crude product was recrystallized from EtOAc to give 1.40 g (37% yield) of pure trimethylacetamide.

Synthesis of N-(4-Pyridyl) Ethyl Succinamate (11). To a solution of 4-aminopyridine (1.50 g, 16.0 mmol) in $CH_2Cl_2$ (50 mL) was added triethylamine (3.50 mL, 25.0 mmol) and ethyl-4-oxo-4-chlorobutyrate (2.25 mL, 16.0 mmol). The resulting mixture was allowed to stir for 1.5 h before being poured into saturated aqueous $NaHCO_3$. The mixture was stirred for 5 min then the layers were separated. The aqueous layer was extracted twice more with $CH_2Cl_2$. The combined organic layers were dried ($Na_2SO_4$) and concentrated. The crude product was recrystallized from EtOAc/hexanes to give 590 mg (17% yield) of pure succinamate.

Synthesis of N,N'-(4-Pyridyl) Urea (12). A mixture of 4-aminopyridine (3.00 g, 31.9 mmol) and carbonyldiimidazole (5.17 g, 32.0 mmol) in benzene (50 mL) was refluxed for 5 h. The reaction mixture was concentrated and the crude product was recrystallized from $H_2O$ to give 1.60 g(47% yield) of pure urea.

Synthesis of N,N'-(3,4-Pyridyl) Urea (13). A mixture of 3,4-diaminopyridine (2.50 g, 23.0 mmol) and carbonyldiimidazole (7.50 g, 46.0 mmol) in benzene (50 mL) was refluxed for 4 h before being poured into $H_2O$. The resulting mixture was acidified with 1.0 M HCl and the layers were separated. The pH of the aqueous layer was adjusted to ~40 wit saturated aqueous $NaHCO_3$ then the solution was concentrated. The solid products were dried under high vacuum for 16 h then were slurried with hot MeOH. The slurried mixture was filtered and the filtrated was concentrated. The crude product was recrystallized from $H_2O$ to give 2.63 g (85% yield) of pure urea.

Synthesis of P,P-Diphenyl N-(4-Pyridyl) Phosphinamide (14). To a solution of 4-aminopyridine (1.00 g, 10.6 mmol) in $CH_2Cl_2$ (30 mL) was added triethylamine (1.70 mL, 12.0 mmol) and diphenylphosphinic chloride (2.00 mL, 10.6 mmol). The reaction mixture was allowed to stir for 6 h before being poured into saturated aqueous $NaHCO_3$. The resulting mixture was stirred for 15 min then the layers were separated. The aqueous layer was extracted twice more with $CH_2Cl_2$. The combined organic layers were dried ($Na_2SO_4$) and concentrated. The crude product was recrystallized from $MeOH/H_2O$ to give 2.69 g (86% yield) of pure phosphinamide.

Synthesis of 4-Pyridinyl Phosphoramidic acid, Diphenyl Ester (15). To a solution of 4-aminopyridine (1.00 g, 10.6 mmol) in $CH_2Cl_2$ (30 mL) was added triethylamine (2.20 mL, 16.0 mmol) and diphenylchlorophosphate (2.30 mL, 11.0 mmol). The reaction mixture was allowed to stir for 3 h before being poured into saturated aqueous $NaHCO_3$. The resulting mixture was stirred for 15 min then the layers were separated. The aqueous layer was extracted twice more with $CH_2Cl_2$. The combined organic layers were dried ($Na_2SO_4$) and concentrated. The crude product was recrystallized from $MeOH/H_2O$ to give 1.36 g (39% yield) of pure phosphoramidic acid diester.

Unless indicated otherwise, the pressure of each of the above reactions is not critical. Generally, the reactions will be conducted at a pressure of about one to about three atmospheres, preferably at ambient pressure (about one atmosphere).

Compounds of the formula (I) which are basic in nature are capable of forming a wide variety of different salts with various inorganic and organic acids. Although such salts must be pharmaceutically acceptable for administration to animals, it is often desirable in practice to initially isolate a compound of the formula (I) from the reaction mixture as a pharmaceutically unacceptable salt and then simply convert the latter back to the free base compound by treatment with an alkaline reagent, and subsequently convert the free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent such as methanol or ethanol. Upon careful evaporation of the solvent, the desired solid salt is obtained.

The acids which are used to prepare the pharmaceutically acceptable acid addition salts of the base compounds of this invention are those which form non-toxic acid addition salts, i.e., salts containing pharmacologically acceptable anions, such as hydrochloride, hydrobromide, hydroiodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate and pamoate [i.e., 1,1'-methylene-bis-(2-hydroxy-3-naphthoate)] salts.

Those compounds of the formula (I) which are also acidic in nature are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the herein described acidic compounds of formula (I). These non-toxic base salts include those derived from such pharmacologically acceptable cations as sodium, potassium, calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum product yields.

The compositions of the present invention may be formulated in a conventional manner using one or more pharmaceutically acceptable carriers. Pharmaceutically acceptable earners that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as prolamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques.

Preferably, the compositions are administered orally, intraperitoneally, or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyothylated versions. These oil solutions or suspensions may also contain a long-chain alcohol diluent or dispersant, such as Ph. Helv or similar alcohol.

The pharmaceutical compositions of this invention may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of novel pyridine of the instant invention that may be combined with the carrier materials to produce a single dosage form will vary depending upon the host treated, the particular mode of administration. Preferably, the compositions should be formulated so that a dosage of between about 5–100 mg/kg, more preferably about 10–50 mg/kg body weight/day of the novel pyridine can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease or injury being treated.

According to an alternate embodiment, the invention provides a method of administering a novel pyridine compound and a neurotrophic agent in a single dosage form or in separate, multiple dosage forms. If separate dosage forms are utilized, they may be administered concurrently, consecutively or within less than about 12 hours, more preferably within less than about 8 hours of one another, depending upon the bioavailability and pharmacokinetics of the agents.

Preferably, the methods of this invention are used to restore nerve impulse conduction through nerve tissue lesions in a patient.

The methods and compositions of this invention may be used to treat nerve damage caused by a wide variety of diseases or physical traumas. These include, but are not limited to, Alzheimer's disease, Parkinson's disease, ALS, stroke and ischemia associated with stroke, neural paropathy, other neural degenerative diseases, motor neuron diseases, sciatic crush, spinal cord injuries and facial nerve crush. The compounds of the invention may be administered alone or as part of a combination therapy. If a combination of active agents is administered, then they may be administered simultaneously, separately, or sequentially.

Figure 1:
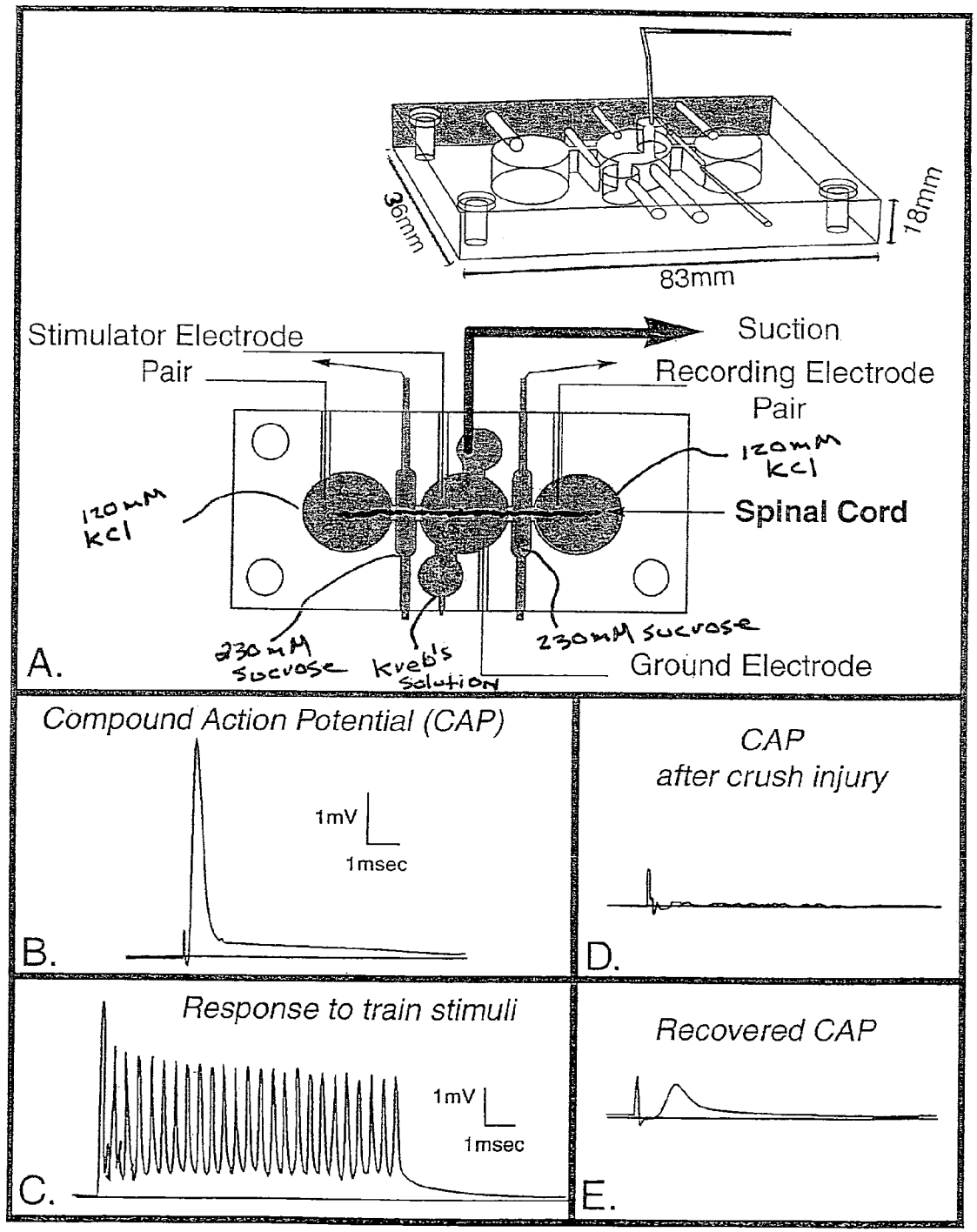
FIG. 1 illustrates (i) a double sucrose gap isolation and recording chamber used to test compound action potential propagation through a standardized crush lesion to strips of guinea pig spinal cord white matter in organ culture (section A), (ii) a single elicited CAP (section B), (iii) a number of repetitive CAPs (section C), (iv) CAP conduction through the cord after being subjected to standardized crush injury (section D), and (v) a CAP beginning to reappear after pharmacological intervention.

II. In Vitro Testing for Recovery of Nerve Impulse Conduction in Response to the Novel Pyridines In vitro screening of novel pyridines of the instant invention for potential therapeutic value demonstrated their effectiveness in restoring nerve impulse conduction through damaged regions of the spinal cord white matter (comprised solely of nerve fibers). To merit advancement to in vivo testing, any compound in aqueous solution applied to the cord damaged in isolation should reveal such partial recovery of compound action potential conduction within at least 15 minutes after application Shi R, Pryor J D (2002), Pathological changes of isolated spinal cord axons in response to mechanical stretch, Neuroscience 110:765–77. Referring to FIGS. 1 and 6, in vitro testing of the novel pyridines using the double sucrose gap isolation and recording chamber (defined previously) satisfied this criterion. Such compound effectiveness in restoring nerve impulse conduction was determined by testing compound action potential propagation through a standardized crush lesion to strips of guinea pig spinal cord white matter in organ culture.

As previously disclosed, the biological basis for the loss of behavior after spinal cord injury is the interruption of nerve impulse "traffic" ascending the cord to the brain from nerve "inputs" from the body, and the reverse—loss of impulse traffic arising in the brain "descending" the spinal cord to targets in the body. Thus, this test vehicle is a first evaluation of the crucial and relevant biological basis for paralysis.

Double Sucrose Gap In Vitro Recording: Now referring to FIG. 6, this figure shows the double sucrose gap recording and isolation chamber. The entire spinal cord of a guinea pig is quickly dissected from the deeply anesthetized animal (see below) and placed in buffered, aerated Krebs solution until use. Prior to mounting in the chamber, the cord is usually split lengthwise to isolate a long strip (ca. 38–40 mm) of predominately white matter which is then mounted in the chamber. There are three large compartments which contain different bathing media: a central one in which oxygenated Krebs solution is continuously pumped and withdrawn (by aspiration) and two end chambers filled with isotonic KCl. The length of the spinal cord spans all three chambers along with two small reservoirs located in-between the chambers. These small reservoirs contain sucrose which is continuously pumped and aspirated. The sucrose helps to electrically isolate the ends of the cord from the center section in a physiological solution. Stimulation at one end of the spinal cord produces compound action potentials (CAPs) that are conducted through the white matter to be recorded at the other end of the chamber. It is the electrical isolation of the ends, permitted by the flowing sucrose, and the fact that the ends of the cord segment are closer to intracellular potential than the center (at extracellular potential) that provides unexcelled resolution of CAPs. Furthermore, continuous monitoring of the compound membrane potential (gap potential) can also be followed during the course of each experiment.

Typically the spinal cord is allowed to stabilize in the recording chamber for about 1 h in order to produce a characteristic response to electrical stimulation. Subsequently the cord is stretched in its center (in the central chamber) using an impactor at about 1.5 m/s. This stretches the spinal cord in a standardized fashion. The stretching induces a transitory loss in CAP propagation across the lesion, which improves with time. Once spontaneous recovery produces a stable "recovery CAP", drug is added to the medium bathing the central chamber. Recording of CAPs is continuous, however about 0.5 h is required for the drug induced changes in amplitude to stabilize. This response is reported as an increase (or decrease) in the "pre-drug" recovered potential (which is normalized to 100%). Subsequently the drug is washed out of the chamber, and the cord's lesion exposed to fresh aerated Krebs solution for approximately 1 h prior to obtaining "post-drug" electrical recordings.

Still referring to the double sucrose gap recording and isolation chamber, FIG. 1, Section A, illustrates features of a slightly different embodiment of this apparatus. In particular, a schematic 3D drawing at the top right of FIG. 1 shows its dimensions—the chamber is fashioned from clear Plexiglas. Below the schematic 3D drawing the four compartments are diagrammed and labeled according to the solutions that are pumped into them. These solutions are drawn off by aspiration, producing a modest, but continuous, flow of media using a capillary pump (not shown). The outside compartments are at or near intracellular potential while the middle chamber (containing a balanced physiological organ culture solution) is at extracellular potential. Therefore, the inversion of the membrane potential during a nerve impulse episode is directly measured in a similar manner to "single" unit intracellular electrophysiological recordings—producing an increase in resolution of the Compound Action Potential (CAP).

The CAP is produced by the synchronous firing of individual nerve fibers (called axons) numbering in the tens of thousands spanning the length of the guinea pig spinal cord. The cord is stimulated to synchronously "fire" CAPs on one side of the chamber (in the example shown, the left side) and the arrival of the CAPs are recorded on the right end. Mixing of the two different solutions is greatly reduced by a swiftly flowing boundary of sucrose through the indicated chambers, which also electrically isolates the ends of the spinal cord segment which spans the entire width of the chamber. The physiological solution (Krebs') is also pH stabilized and oxygenated in the reservoir that provides the media pumped though the middle chamber. This increases, and ensures, the viability of the cord during physiological measurements. Carefully dissected ca. 40 mm long segments of cord can be maintained in the chamber—functioning normally (as shown by nerve impulse conduction) for up to two days. A single elicited CAP is shown in Section B, and a number of repetitive CAPs (produced by a train of repeated stimulations) in Section C. Such records are indicative of intracellular, single nerve fiber recordings, and this level of resolution is approximately 100 times better than conventional means of measuring CAPS by extracellular recording techniques.

Compound nerve impulse (CAP) conduction though the cord following a standardized crush injury to the cord in its, middle—that is—in the central physiological compartment is shown in Section D. The passage of the nerve impulses stimulated on the left side reaches the injury and is blocked—failing to traverse the chamber to be recorded on the right side.

Referring to FIG. 1, Section F, a CAP is beginning to reappear after pharmacological intervention: the compound of the instant invention was introduced into the physiological solution bathing the injury site in the middle compartment, i.e. the compartment containing Kreb's solution. The most precise means of comparing the quantitative aspects of recovery of nerve impulse conduction is to compute the derivative of the magnitude and duration of the CAP (i.e., the "area under the curve") for comparison of the pre-injury values to those values produced by the introduction of a "test" drug.

III. In Vivo Testing

During live animal testing using guinea pigs, novel pyridine derivatives of the instant invention were administered through a gastric tube to large adult guinea pigs which had previously received a standardized compression injury to their mid-thoracic spinal cords. The ability of these compounds to restore conduction in this second technique was determined by a quantitative evaluation of SSEPs. The following protocols and routes of administration were employed.

Prior to spinal cord injury, fully adult guinea pigs (Hartly strain, around 400 g) were lightly sedated with an intramuscular injection of Ketamine/Rompum and rendered immobile during the placement of stimulation and recording electrodes as illustrated in FIG. 2. A series of SSEP records were then taken subsequent to both tibial and median nerve stimulation in this normal animal. It should be noted here that all surgical procedures and physiological recordings were carried out on anesthetized animals. All animal studies were carried out under protocols approved by the University Animal Care and Use Committee, under strict adherence to University, State, and Federal guidelines for the use of animals in research.

Subsequently, a dorsal laminectomy surgical procedure was carried out exposing the dorsal (posterior) region of the mid-thoracic spinal cord within the vertebral column, the tough covering of the spinal cord (the dura) incised and removed, and the cord crushed by a standardized technique (constant displacement compression. Blight A R (1991a), Morphometric analysis of a model of spinal cord injury in guinea pigs, with behavioral evidence of delayed secondary pathology, J Neurol Sci 103:156–171,; Borgens R B, Shi R, Bohnert D (2002), Behavioral recovery from spinal cord injury following delayed application of polyethylene glycol, J Exp Biol 205:1–12, both incorporated herein by reference.

Within 5–10 minutes of this procedure, another set of SSEP records were taken—demonstrating in every case the complete elimination of SSEPs while also revealing a positive control procedure (median nerve stimulation) This "flatline" record proved the injury, to the cord, to be severe and to compromise all ascending functions revealed by the elimination of the SSEP.

All animals were allowed to recover, heal, and were not used again for surgical experiments until 2 months post injury. However, periodically physiological records were taken to monitor their status—and a final record at around 2 months post injury to confirm the chronic loss of ascending SSEP conduction through the mid-thoracic lesion.

After 8 weeks had elapsed and a "pre-drug application" electrical record obtained, the guinea pigs were lightly sedated and a test compound was administered directly into the stomach by a gastric tube (compounds were undissolved during introduction to the stomach, however, the gastric tube and any remnants of the compounds were flushed into the stomach by secondary introduction of less than 1 ml of distilled water).

Electrical recordings of SSEP were begun thereafter, and were taken every hour for a 5 to 6 hour period post-treatment.

Blood samples were obtained at these various times and were frozen for later determination of the precise plasma level of the compounds by HPLC detection techniques. (This last step allows a more knowledgeable development of compounds for clinical use).

In most instances, drugs were directly administered to the animal's stomach by a gastric tube inserted in the mouth of sedated animals.

Referring to FIG. 2, a normal functioning neural circuit is outlined by the pathway of nerve impulses stimulated in the medial nerve of the foreleg—into the spinal cord, ascending the spinal cord to terminate in evoked potentials measured in the contralateral sensory motor cortex of the brain. Stimulation of the tibial nerve of the leg in an intact (undamaged or normal animal) would produce a similar barrage of evoked potentials arriving at the brain. This is shown as Peak (P) 1 and 2; early and late arriving evoked potentials the top of the actual electrical recordings to the left of the guinea pig. Crushing the spinal cord in between the brain and the hind leg eliminates the transmission of these potentials up the spinal cord. The injury eliminated the appreciation of painful stimuli applied to the foot by the Cortex of the Brain by interrupting the SSEP.

The actual somatosensory evoked potential recording, shown in FIG. 2 on the left, illustrated the complete elimination of evoked potential immediately after such a crush was made (postcrush record). This state of blocked conduction persisted for one continuous month of testing in this animal. The bottom record shows a median nerve control procedure performed at one month in this spinal cord injured animal proving that evoked potentials could be measured at the brain had they not been eliminated by the injury.

The neural circuit, simplified in the insert in the right of FIG. 2, shows an electrical stimulation applied to the hindpaw—actually to the tibial nerve—which would normally produce evoked potentials ascending the foot and cord to the brain. This was interrupted by a spinal cord injury represented as a break in the cord. It can be established in the laboratory that the elimination of ascending SSEPs recorded from electrodes located at the brain is not an artifact attributable to a control procedure. In the experiments that generated the data reflected in FIG. 2, the forepaw was stimulated (actually the median nerve of the foreleg) producing SSEPs that ascended the cord to the brain- because this neural circuit was not interrupted by the local spinal cord damage (i.e. it was "above" the level of the injury).

On the left of FIG. 2, actual physiological records of SSEPs are shown (in the inset marked C). Each waveform is an average of 200 repetitive stimulations of the relevant nerves in the hind or forepaw. At the top a normal SSEP is shown—recorded at the sensory cortex—in response to stimulation of the hind paw's tibial nerve. It should be noted that there are two SSEP peaks shown (P 1 and P 2). P 1 is an early arriving evoked potential (recorded ca. 24 msec after stimulation), and P 2 is later arriving (about 60 msec after stimulation). This is because fast and slow conducting fibers and synapses segregate into peaks of different latencies as they ascend the spinal cord to the brain. A crush to the mid-thoracic spinal cord eliminated recording of the SSEP (post crush record)—which did not recover during 1 month of continuous monitoring in this individual animal. The bottom record shows a control SSEP (median nerve stimulation) proving that the inability to record a SSEP was not due to any other variable but the damage to the spinal cord.

Now turning to a slightly different protocol, large (>350 gm) adult female guinea pigs were sedated (sodium pentobarbital, see below) and a normal regimen of somatosensory evoked potential (SSEP) testing was carried out in the intact animal. This included recording evoked potentials from the sensorimotor cortex in response to stimulation of first (usually) the median nerve of the contralateral fore limb and the median nerve of the contralateral hind limb. After these baseline records were obtained, animals were deeply anesthetized, the spinal cord surgically exposed and crushed by a standardized technique (see Surgery below). Within an hour, a second set of electrical records was obtained, demonstrating the loss of conduction of evoked potential conduction through the fresh lesion. It was important to first establish that the neural circuit above the level of the crush injury was intact and normal SSEPs could be recorded subsequent to medial nerve stimulation in this animal, which constitutes an internal control on SSEP recording procedures (see FIG. 7).

Figure 7:
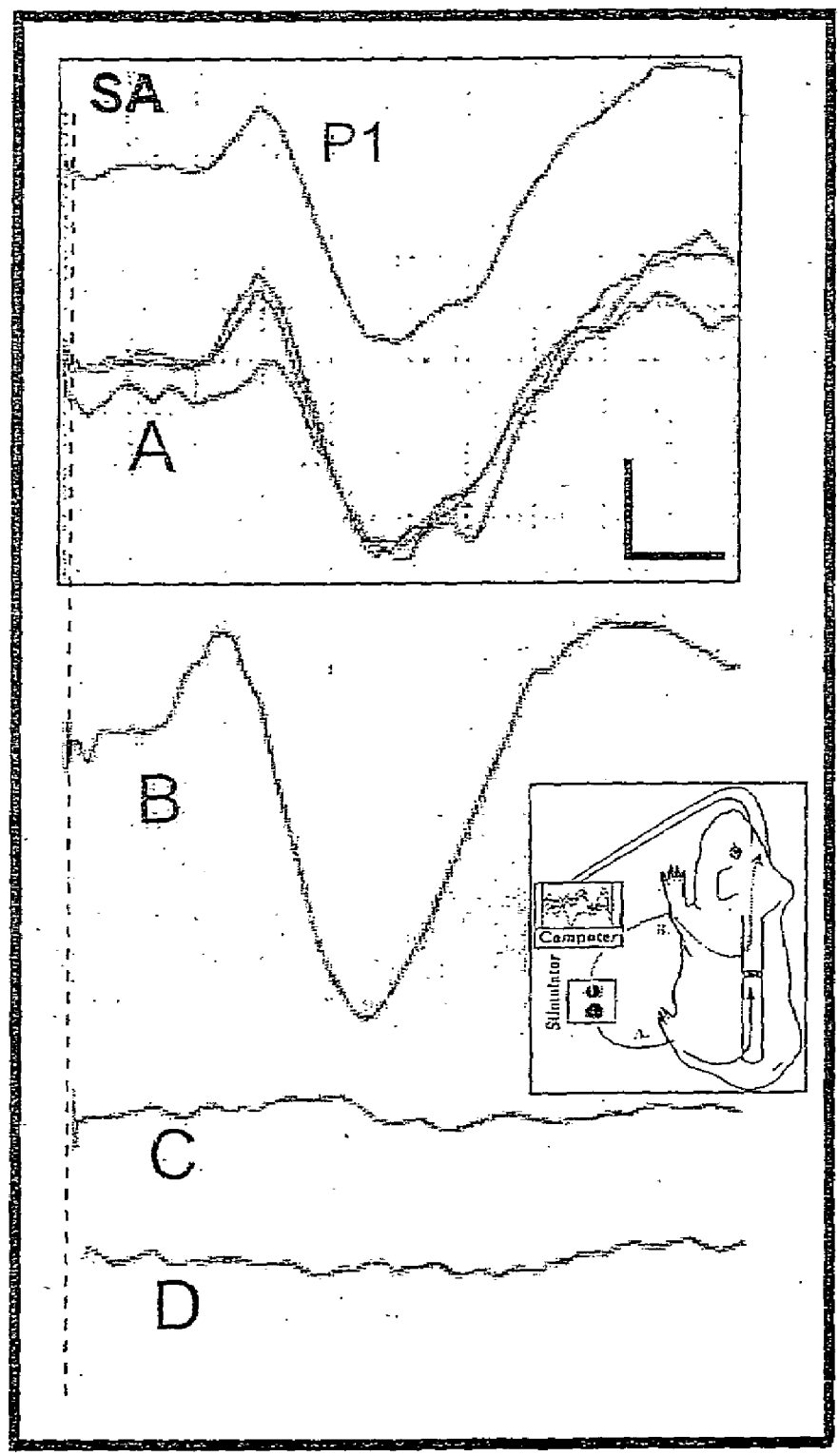
FIG. 7 illustrates the measurement of SSEP's in a sedated guinea pig.

Referring to FIG. 7, record A is an unedited electrical record of early arriving evoked potentials ascending the spinal cord in response to stimulation of the tibial nerve (peak 1; P 1). The bottom three traces are individual trains of the 200 stimulations. The single trace above, along with records B–D, is the averaged waveform. This record was obtained from a sedated guinea pig prior to spinal cord compression. In B, the waveform, taken one hour after spinal cord compression, shows a control stimulation of the medial nerve of the forelimb in the same animal. Note the large amplitude of the early arriving EP. In C, the complete loss of SSEP conductance through the spinal cord lesion is revealed subsequent to stimulation of the tibial nerve of the hind limb at the same time and in the same animal. This complete loss in the ability of ascending volleys of compound action potentials to be conducted through damaged spinal cord white matter is still obvious 1 week later in this animal (D). Such records are characteristic of all animals used in this report.

Similar to FIG. 2 the drawing of the guinea pig in FIG. 7 shows the control circuit activated by stimulation of the medial nerve. The neural circuit activated by stimulation of the tibial nerve of the hind limb is shown to be interrupted by damage to the spinal cord.

After these records were obtained, the animals recovered from anesthesia and were maintained for 1 week. Another set of evoked potentials were recorded to establish the extent of the remaining conduction deficit ~1 week post injury. After these records were taken, animals were administered either 4-AP, which was used as a standard, or one of the derivatives by gavage. The effect that the drugs had on conduction was then monitored at t=30 min, 1 hour, and then hourly up to 4 hours. After the period of recording was concluded, the animals were allowed to recover and then were returned to their cages. A final set of records was obtained the next day (~18 h later) then the animal was euthanized.

Surgery. A conventional constant displacement injury is favored over a constant impact as a means to reduce the variability of behavioral and anatomical consequences of the injury. This conventional method is described in Borgens, R. B.; Shi, R.; Bohner, T. D. Behavioral Recovery from Spinal Cord Injury Following Delayed Application of Polyethylene Glycol. *Journal of Experimental Biology* 2002, 205, 1–12: Blight, A. R. Morphometric analysis of a model of spinal cord injury in guinea pigs, with behavioral evidence of delayed secondary pathology. *J. Neurolog. Sci.* 1991, 103, 156–171, both of which are incorporated herein by reference.

Briefly: Adult guinea pigs (>~350 g; Hartley Strain) were anesthetized by an intramuscular injection of 100 mg/kg ketamine HCl and 20 mg/kg xylazine. A dorsal laminectomy procedure exposed the spinal cord at about the 12$^{th}$ thoracic vertebral level (T12) to the first lumbar level (L1). The exposed cord was crushed using a specially modified forceps possessing a détente. To immobilize animals for electrical records, a more gentle sedation was produced by intramuscular injection (0.1 cc sodium pentobarbital, 50 mg/ml). At the end of the study, while the animals were under anesthesia, the guinea pigs were euthanized by increasing the anesthetic dose significantly, followed by perfusion/fixation (glutaraldehyde in phosphate buffered Ringer's solution).

SSEPs. It is the loss of nerve impulse conduction through the white matter of the spinal cord lesion that is associated with the catastrophic deficits in behavior observed in SCI. These volleys of compound nerve impulses ascending and descending the spinal cord are associated with numerous axons and synapses, and are referred to as "evoked potentials" (EP) when stimulated synchronously by electrical activation of a compound nerve of the lower or upper limbs (in the SSEP) or activation of the cortex (during motor evoked potential recording, or MEPs, not performed here). This form of stimulation of largely ascending impulses—then recording them at the contralateral sensorimotor cortex of the brain is referred to as somatosensory evoked potential testing (SSEP).

Stimulation of the tibial nerve of the hind limb was accomplished using a pair of needle electrodes inserted near the nerve at the popliteal notch of the knee. Similar SSEPs were evoked by stimulation of the median nerve of the forelimb with pair of stimulation electrodes. Recording electrodes were located in the scalp covering the contralateral cortex region, with an indifferent electrode usually located in the pinna of the ear.

A complete electrical record for one period of investigation involved stimulating the nerve 200 times in a train (2 mA square wave, 200 μsec duration at 3 Hz; see section A of FIG. 7). Three to four sets of these records were then averaged to produce a single waveform for quantitative study as shown in sections A and B of FIG. 7. Recording and stimulation used a Nihon Kohden Neuropak 4 and a Power Mac G-3 computer.

Quantitative evaluation involved measurements of latency from the initiation of stimulation (noted by the stimulus artifact) to the initiation of the EP, however, the most reliable and informative comparative data involved a determination of the area beneath the EP in pixels using IPLab™ spectrum software (Scanalytics, Farifax, Va.). These areas beneath the peak waveform (that is above baseline) were normalized by dividing the post injury (or post treatment) EP by the area of the initial EP recorded in the normal animal. If all (100%) nerve fibers normally fired in synchrony by the stimulation regimen before injury were theoretically recruited into conduction after a treatment, the average SSEPs should thus reach unity (1.0).

Drug Administration: Drugs were administered by gavage using the following methods. All tested drugs were introduced in solution (see below) into the guinea pig stomach using a round tipped feeding needle (either 18 gauge, 55 mm length or 16 gauge, 75 mm length; Fine Science Tools). Gavage is only carried out on the sedated animal. In guinea pigs, the soft palate is continuous with the base of the tongue with only a small opening to pass the tube. The feeding needle is advanced between the incisors and the beginning of the molars, which initiates a swallowing or gag reflex, facilitating advancement of the feeding needle to the stomach. Prior to this operation, the correct needle (sized relative to the size of the guinea pig) is marked by placing its end adjacent the animal's last rib and marking the proximal portion of the needle near the tip of the nose. This provides an estimate of the required length to advance to the stomach during gavage. The needle can be connected to either a syringe or an aspirator allowing material to be introduced into, or withdrawn from, the stomach.

Dosage and weight data: A starting dosage for guinea pigs was estimated by working within the range of 4-AP given in clinical cases of paraplegia in dogs (0.5–1.0 mg/kg body weight). In the case of an approx. 500 g guinea pig, this would result in a total dosage of about 0.25 g. A stock solution for gavage was prepared where 0.2 cc of an aqueous solution contained 0.2 mg 4-AP. This allowed the relative standardization of total concentration given to animals, and was facilitated by the lack of significant variation in their weights (for the ten animals that were tested with 4-AP the mean weight was 421.5±20.9 g; for methyl carbamate 3 the mean weight was 411.6±23 g; $P \geq 0.5$). The effective dosage for 4-AP was sufficient to produce an improvement in the electrophysiological record equal to 0.47±0.04 mg/kg. By comparison, the effective dosage for carbamate 3 appeared to be slightly lower (0.37±0.2 mg/kg) but this difference was not statistically different given the small sample size ($P \geq 0.05$).

IV. Results

In vitro Testing of Conduction through Guinea Pig Spinal Cord

The (methylamino)pyridines, amides and ureas, shown below, all failed to produce any enhancement in the recovery CAP amplitude at the same effective concentration as 4-AP.

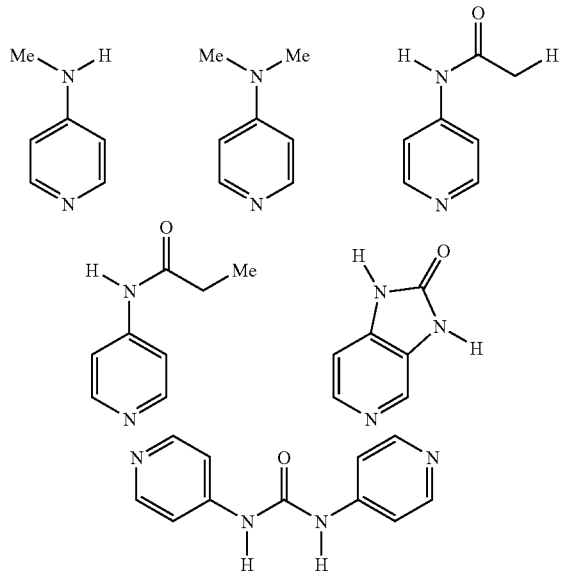

Figure 8:
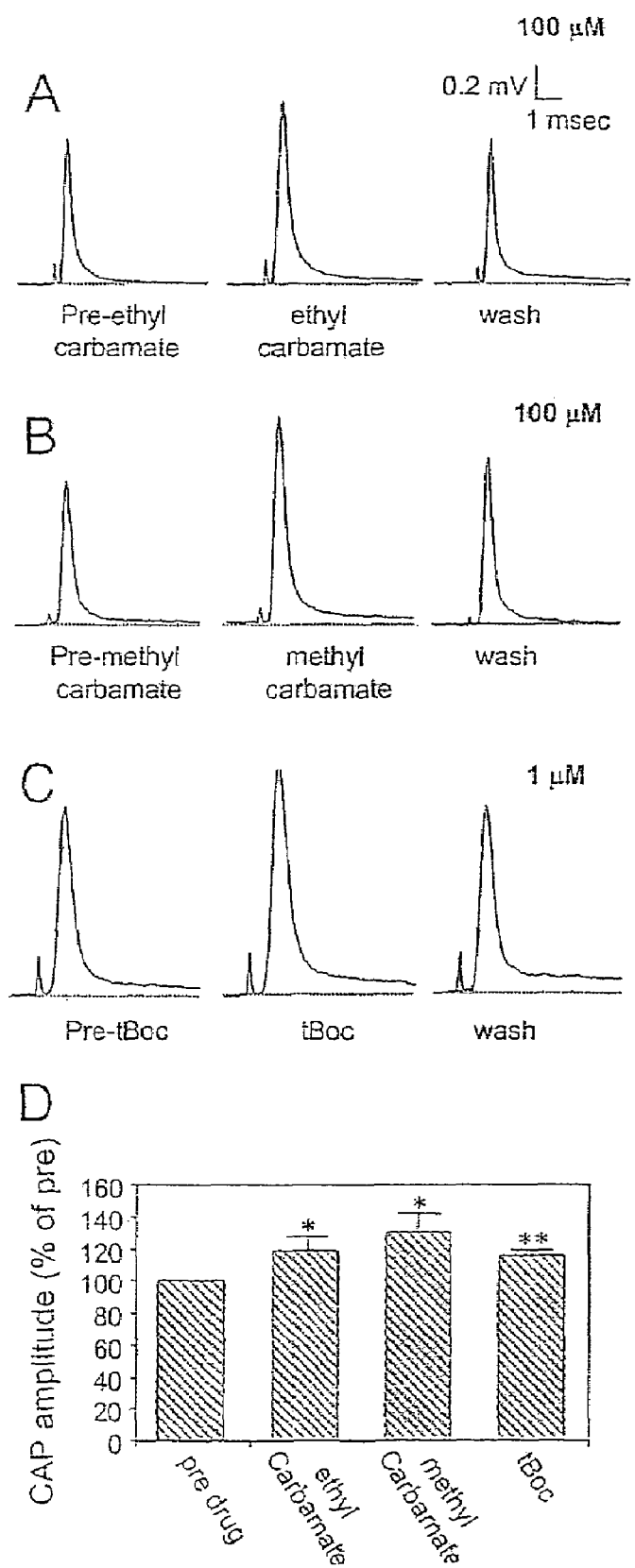
FIG. 8 illustrates responses of recovered compound nerve impulses to in the presence of compounds of the present invention.

Three compounds, N-(4-pyridyl) methyl carbamate (3); N-(4-pyridyl) ethyl carbamate (2) and N-(4-pyridyl) t-butyl carbamate (1), all revealed varying ability to restore conduction through injured spinal cord. Pilot trials with these three carbamates established that working concentrations equal to or below that of 4 AP (100 μM) were capable of producing a reproducible recovery of conduction in the double sucrose gap recording chamber. Methyl carbamate (3) and ethyl carbamate (2) were found to behave similarly to 4-AP, producing recovery of CAP conduction at a concentration of approximately 100 μM in the absence of toxicity. Toxicity in these in vitro trials was defined as the significant reduction of the CAP. t-Butyl carbamate (1), on the other hand, was found to be toxic to white matter at 100 μM when added to the bathing solution. It was found, however, that carbamate (1) reproducibly enhanced CAP conduction through the lesion, in the absence of toxicity, at a much lower effective concentration (1 μM) than is seen with 4-AP. For methyl carbamate (3), an effective concentration of 100 μM produced an increase in the amplitude of the recovered CAP averaging 30.6±11.7% (n=4). For ethyl carbamate (2), the increase was 18.6±8.7% (n=8) at the same concentration. This increase in amplitude was statistically significant ($P \leq 0.04$). After a 1 h wash, the enhanced CAP fell in amplitude to pre-drug levels. t-Butyl carbamate (1) increased the recovery CAP amplitude by 15.4+3.4% at 1 μM (n=5). This increase was very significant relative to the pre-drug CAPs ($P \leq 0.002$). FIG. 8 provides examples of electrical records of CAP enhancement for each of these three drugs and graphically displays these data. In particular, in panel A, the first electrical record shows the recovered compound action potential (CAP) prior to the addition of ethyl carbamate (2) (the initial small wave form is the stimulus artifact). The second record was taken about ½ hour after the addition of carbamate (2). Note the ~20% increase in the amplitude of the CAP. The third record shows that the amplitude of this enhanced CAP has fallen back to pre-drug levels after removal of the drug and an ~30 min wash. Panel B shows a similar set of electrical records obtained after introduction of methyl carbamate (3). Again, the increase in amplitude in the presence of the drug is obvious. This enhancement was only sustained during the administration of the drug and approximate pre-drug levels were measured after a washing out of the drug. Panel C depicts a similar set of records to A and B, using t-butyl carbamate (1). This drug was effective at enhancing CAP amplitudes at much lower concentrations (1 μM). Panel D provides a histogram of all data. Carbamates (3) and (2) statistically enhanced CAP amplitudes at 100 μM concentration ($P \leq 0.04$; one asterisk), while carbamate (1) statistically improved the CAP at 1 μM compared to pre-drug amplitudes ($P \leq 0.002$; two asterisks).

In Vivo Testing in Guinea Pig

Post surgery, SSEPs had been eliminated in all animals by the time electrical records could be accomplished (<1 hour). In all but two animals these 'flat-line" recordings were characteristic of the 1 week recordings as well, indicating there was little evidence for spontaneous recovery of conduction in any of the guinea pigs one week after surgery. In the two exceptions, a small and very early arriving Evoked Potential (EP; approximately 25 msec latency) was noted, however, the magnitude of this peak was barely detectable above baseline and it was not dependably evoked. Therefore, gavage and further recordings were carried out on these animals and their data are pooled with the rest. Gavage of 4-AP and carbamates (3) and (2) was uneventful; however, we were unable to carry out this procedure using the t-butyl carbamate (1). Crystalline carbamate (1) was not tolerated and the initial attempts at producing a solution of known concentration for oral insertions were problematic. As a result, provided herein are only the preliminary in vitro data below for comparison purposes.

4-AP produced a strong and dependable enhancement of EPs within 30 min to 1 hour after insertion as observed by a return of an early arriving EP (over baseline). Two of the ten animals failed to respond to 4-AP by 4 hours after gavage. There were no failures to respond when using the carbamates (1) and (2).

Figure 3:
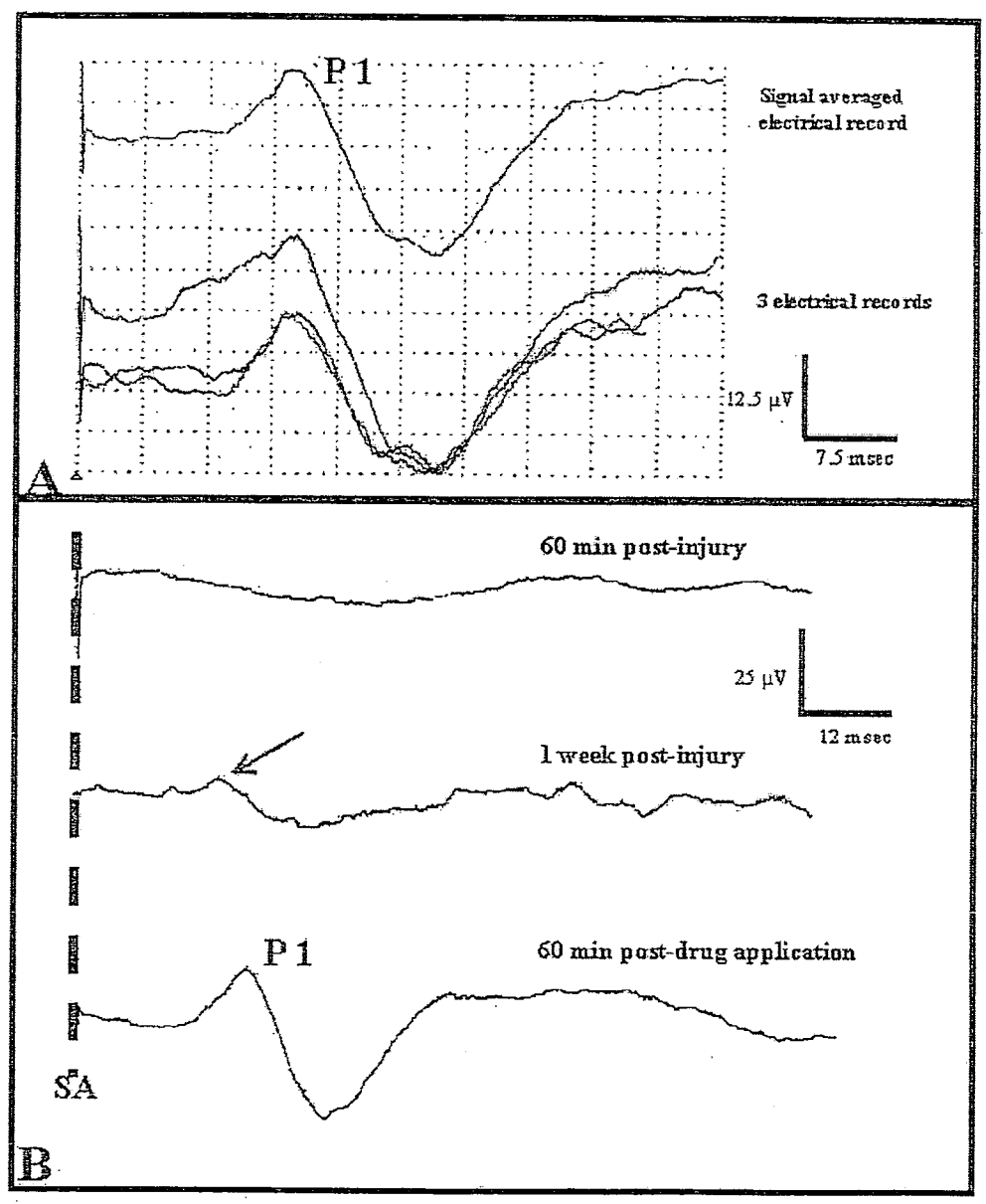
FIG. 3 illustrates an actual, unedited electrical record of a normal SSEP, and shows rapid establishment of a nearly normal cortical potential (P 1) in response to the in vivo administration of N—(4 Pridyl) Methyl carbamate, a compound of the instant invention.

Note that even though the sample size was small, an apparent enhancement of EP recovery by methyl carbamate (1) was demonstrated (see FIG. 3). FIG. 3 shows the, Recovery of spinal cord conduction subsequent to oral administration of N-(4-pyridyl) methyl carbamate (1). In FIG. 3 an unedited electrical record of a normal SSEP is shown in section A. The waveforms were recorded by electrodes located over the sedated guinea pig's sensory cortex after electrical stimulation of the tibial nerve of the hind paw. The bottom 3 records, still in section A, are individual traces of 200 repetitive stimulations of the nerve. The dotted line (SA) marks the stimulus artifact. An early arriving cortical potential is shown, approximately 30 ms after stimulation (marked P 1) in the uninjured guinea pig (A).

In section B, responses to the oral ingestion of the test compound are shown in the same animal providing the record in section A. The top record of section B was made 1 hour after a crush injury to the midthoracic spinal cord as described herein. Note the complete elimination of the cortical potential after stimulation of the tibial nerve of the hind paw. One week later (second trace in section B) this failure to conduct impulses through the spinal cord injury has changed little. The bottom record was made 1 hour after gastric tube administration of N-(4-pyridyl) methyl carbamate (1). Note the rapid establishment of a nearly normal cortical potential (P 1).

Even though the sample size was small, an apparent enhancement of EP recovery by methyl carbamate (1) is demonstrated (FIG. 3). Thus, some statistical comparison between these groups is provided. All data were normalized by dividing the area (expressed as pixels) beneath recovered EP by the same pre-injury data.

The data shows that carbamate (1) significantly enhanced the recovery of EP compared to 4-AP at 1 week post injury. Both two-way ANOVA and a straight forward Student's T test confirmed a significant increase (ANOVA=0.02; two-tailed Student's T=0.47). Given that the latter test is more conservative relative to the small sample size only this comparison is provided in Table 1 below. Note the enhancement of EPs by the methyl carbamate (1) compared to the structurally similar ethyl carbamate (2) (Table 1). The latter carbamate did not meet significance compared to 4-AP data.

TABLE 1

| | Test Compound | n | Mean | SD | SEM | Range | Statistic |
|---|---|---|---|---|---|---|---|
| 1 | 4-AP | 10 | 40.0 | 31.0 | 9.8 | 0–100 | 1 vs. 2, P = 0.47 |
| 2 | Methyl carbamate (1) | 5 | 78.0 | 14.2 | 5.8 | 58–100 | 2 vs. 3, P = 0.003 |
| 3 | Ethyl carbamate (2) | 4 | 41.5 | 13.2 | 6.6 | 27–55 | 1 vs. 3, P = 0.93 |

The three carbamate derivatives of 4-AP (1, 2, and 3) were tested. All three compounds induced an increase in CAP above the pre-drug level, without any indication of toxicity at the concentrations studied. The methyl and ethyl carbamates (3) and (2) were effective at the same concentration as 4-AP (100 μM), although they induced a slightly lower recovery of CAP than 4-AP. The results from t-butyl carbamate (1) were also interesting. Using the concentration that was optimal for 4-AP, this compound proved to be extremely toxic to the spinal cord. However, at 1 μM, 1% of 4-AP's optimal concentration, t-butyl carbamate (1) showed an increase in recovery CAP that was equivalent to the recovery observed for carbamates (3) and (2).

Accordingly, it is clear from the present disclosure that three compounds, methyl carbamate (3), ethyl carbamate (2) and t-butyl carbamate (1) are all capable of enhancing action potential conductance in mechanically injured spinal cord segments. At 100 μM, carbamates (3) and (2) enhanced CAP conduction significantly, whereas t-butyl carbamate, at 1 μM, was able to enhance CAP conduction significantly.

It is to be understood by those skilled in the art that the foregoing description and examples are merely illustrative of the present invention, and should in no way be interpreted as limiting the scope of the present invention. Variations of the detail presented herein may be made without departing from the spirit and scope of the present invention as defined by the following claims.

What is claimed is:

1. A method of treating a mammal suffering from injured mammalian nerve tissue, the method comprising the step of administering to the mammal in need thereof, a pharmaceutical composition, or pharmaceutically acceptable salt, comprising a compound selected from the group consisting of:
   N-(4-Pyridyl) t-Butyl Carbamate;
   N-(4-Pyridyl) Ethyl Carbamate;
   N-(4-Pyridyl) Methyl Carbamate; and
   N-(4-Pyridyl) Isopropyl Carbamate.

2. A method of treating a mammal suffering from injured mammalian nerve tissue, the method comprising the step of administering to the mammal in need thereof, a pharmaceutical composition, or pharmaceutically acceptable salt, comprising a compound selected from the group consisting of:
   N-(4-Pyridyl) t-Butyl Carbamate;
   N-(4-Pyridyl) Ethyl Carbamate;
   N-(4-Pyridyl) Methyl Carbamate; and
   N-(4-Pyridyl) Isopropyl Carbamate: wherein the mammalian nerve tissue was injured as a result of trauma, disease, traumatically-induced compression, tumors, hemorrhage, infectious processes, spinal stenosis a, or impaired blood supply.

3. The method of claim 2, wherein administration of the pharmaceutical composition restores action potential or nerve impulse conduction through a mammalian nerve tissue lesion.

4. The method of claim 1, wherein the injured mammalian nerve tissue is CNS or PNS tissue.

5. The method of claim 4, wherein the injured mammalian nerve tissue is spinal cord tissue and the mammal is a human.

6. The method of claim 1, wherein the compound, or pharmaceutically acceptable salt thereof, in the pharmaceutical composition functions as a neurotrophic factor.

7. The method of claim 1, wherein the pharmaceutical composition displays the restoration of action potential or nerve impulse conduction through a mammalian nerve tissue lesion when administered to spinal cord tissue in vitro.

8. A method of treating a mammal having a spinal cord injury, the method comprising the steps of:
   a. administrating a pharmaceutical composition comprising a N-(4-Pyridyl) Carbamate or a pharmaceutically acceptable salt thereof to a mammal having a spinal cord injury in an effective dose for treating the spinal cord injury, wherein the effective dose for the pharmaceutical composition is lower than a therapeutic dose of 4-aminopyridine in the same mammal for the same injury;
   b. wherein the N-4 Pyridyl Carbamate displays activity in restoration of action potential conduction through a spinal cord lesion when administered to a spinal cord tissue in vitro; and
   c. wherein the N-4-Pyridyl Carbamate is N-(4-Pyridyl) t-Butyl Carbamate, N-(4-Pyridyl) Ethyl Carbamate, N-(4-Pyridyl) Methyl Carbamate or N-(4-Pyridyl) Isopropyl Carbamate.

9. The method of claim 8, wherein the therapeutic dose is between approximately 0.2 mg of the pharmaceutical composition per kilogram of the mammal and approximately 1.0 mg of the pharmaceutical composition per kilogram of the mammal.

10. The method of claim 9, wherein the therapeutic dose is between approximately 0.3 mg of the pharmaceutical composition per kilogram of the mammal and approximately 0.6 mg of the pharmaceutical composition per kilogram of the mammal.

* * * * *